United States Patent
Kishi et al.

(10) Patent No.: US 11,291,425 B2
(45) Date of Patent: Apr. 5, 2022

(54) UTENSIL FOR EVALUATING LENGTH MEASUREMENT ERROR IN X-RAY CT DEVICE FOR THREE-DIMENSIONAL SHAPE MEASUREMENT

(71) Applicants: Shimadzu Corporation, Kyoto (JP); NATIONAL INSTITUTE OF ADVANCED INDUSTRIAL SCIENCE AND TECHNOLOGY, Tokyo (JP)

(72) Inventors: Taketo Kishi, Kyoto (JP); Makoto Sato, Kyoto (JP); Toshiyuki Takatsuji, Ibaraki (JP); Makoto Abe, Ibaraki (JP); Hiroyuki Fujimoto, Kyoto (JP)

(73) Assignees: SHIMADZU CORPORATION, Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 416 days.

(21) Appl. No.: 16/485,639

(22) PCT Filed: Mar. 27, 2018

(86) PCT No.: PCT/JP2018/012546
§ 371 (c)(1),
(2) Date: Aug. 13, 2019

(87) PCT Pub. No.: WO2018/193800
PCT Pub. Date: Oct. 25, 2018

(65) Prior Publication Data
US 2021/0282734 A1 Sep. 16, 2021

(30) Foreign Application Priority Data
Apr. 21, 2017 (JP) .............................. JP2017-084774

(51) Int. Cl.
*A61B 5/08* (2006.01)
*A61B 6/00* (2006.01)
(Continued)

(52) U.S. Cl.
CPC .............. *A61B 6/583* (2013.01); *A61B 6/032* (2013.01); *A61B 90/06* (2016.02); *A61B 2090/061* (2016.02)

(58) Field of Classification Search
CPC ......... A61B 6/032; A61B 6/5205; A61B 6/54; A61B 6/583; A61B 2090/061;
(Continued)

(56) References Cited

U.S. PATENT DOCUMENTS 6,471,399 B1 * 10/2002 Zylka ..................... A61B 6/583
378/207
2004/0252811 A1 * 12/2004 Morita ................... A61B 6/466
378/207
(Continued)

FOREIGN PATENT DOCUMENTS

JP 2008-180557 A 8/2008
JP 2014-190933 A 10/2014
JP 3206123 U 9/2016

OTHER PUBLICATIONS

International Search Report and Written Opinion dated Jun. 5, 2018 in corresponding application No. PCT/JP2018/012546; 8 pgs.
(Continued)

*Primary Examiner* — Irakli Kiknadze
(74) *Attorney, Agent, or Firm* — Maier & Maier, PLLC

(57) ABSTRACT

In order to sufficiently capture spatial distortion specific to an X-ray CT device and evaluate the three-dimensional shape measurement accuracy of the X-ray CT device, in a utensil, by attaching support rods fixing spheres to the tip thereof and having different lengths to a base spheres are
(Continued)

arranged in an XYZ space on the base. On a flat surface on the top of the base, the support rods supporting the spheres and having different lengths are arranged at predetermined intervals. In doing so, the spheres are arranged in the XYZ space respectively at appropriate inter-sphere distances.

18 Claims, 15 Drawing Sheets

(51) Int. Cl.
*A61B 90/00* (2016.01)
*A61B 6/03* (2006.01)

(58) Field of Classification Search
CPC ......... A61B 90/06; A61B 6/03; A61B 6/4233; A61B 6/5252; A61B 6/5258; A61B 6/585; A61B 2017/00725; A61B 2017/00809; A61B 2034/105; A61B 2034/107; A61B 2034/2051; A61B 2034/2055; A61B 2034/2059; A61B 2034/2061; A61B 2034/207; A61B 6/037; A61B 6/4028; A61B 6/4258; A61B 6/4291; A61B 6/4488; A61B 6/502; A61B 6/548; A61B 17/22; A61B 17/22012; A61B 2017/00876; A61B 2017/22084; A61B 34/73; A61B 2017/22094; A61B 2034/733; A61B 17/15; A61B 17/1746; A61B 17/12022; A61B 2090/3983; A61B 34/10; A61B 2017/00207; A61B 2034/102; A61B 2034/108; A61B 2034/2065; A61B 6/584; A61B 34/20; A61B 6/582; A61B 6/4441; A61B 6/145; A61B 6/466; A61B 6/481; G01B 15/045; G01B 21/042; G01B 11/255; G01B 15/00; G01B 3/30; G01B 15/02; G01N 2223/1016; G01N 2223/303; G01N 2223/3306; G01N 2223/419; G01N 2223/645; G01N 23/046; G01N 2223/3035; G01N 21/4795; G01N 21/6428; G01N 21/6456; G01N 15/147; G01N 23/083; G01N 15/1475; G01N 21/05; G01N 2223/04; G01T 1/1644; G01T 1/243; G01T 1/244; G01T 1/2928; G01T 7/005; G06T 2207/10081; G06T 11/005; G06T 2207/20182; G06T 2207/30004; G06T 2207/30048; G06T 2207/30096; G06T 2207/30101; G06T 2207/10121; G06T 2207/30204; G06T 7/70; G06T 7/80; A61N 2005/1076; A61N 5/1067; A61N 5/1075; A61N 2005/1061; A61N 5/1049; G05B 19/4015; G05B 2219/45117; G05B 2219/49257; G05B 2219/50132

USPC .............................. 378/4, 19, 205
See application file for complete search history.

(56) References Cited

U.S. PATENT DOCUMENTS

| | | | | |
|---|---|---|---|---|
| 2008/0075227 | A1* | 3/2008 | Christoph | A61B 6/584 378/23 |
| 2008/0154262 | A1* | 6/2008 | Brundobler | A61B 90/50 606/53 |
| 2013/0195239 | A1* | 8/2013 | O'Hare | A61B 6/582 378/4 |
| 2013/0195255 | A1* | 8/2013 | Avila | A61B 6/583 378/207 |
| 2013/0281803 | A1* | 10/2013 | Scheele | A61B 5/1455 600/323 |
| 2014/0153694 | A1* | 6/2014 | Suppes | A61B 6/583 378/62 |
| 2015/0342559 | A1* | 12/2015 | Hilton | A61B 6/583 378/207 |
| 2015/0374327 | A1* | 12/2015 | Singh | A61B 6/035 378/207 |
| 2016/0015356 | A1* | 1/2016 | Baiu | A61B 6/583 378/207 |
| 2017/0020481 | A1* | 1/2017 | Hawker | A61B 6/584 |
| 2017/0112462 | A1* | 4/2017 | O'Hare | G01T 7/005 |

OTHER PUBLICATIONS

D.Weiss, R.Lonardoni A.Deffner, C.Kuhn, Geometric image distortion in flat-panel X-ray detectors and its influence on the accuracy of CT-based dimensional measurements, 4th Conference on Industrial Computed Tomography (iCT), Sep. 19-21, 2012, Wels, Austria (iCT 2012); 7 pgs.

Japanese Office Action dated Sep. 8, 2020, in connection with corresponding JP Application No. 2019-513529 (12 pp., including machine-generated English translation).

Takahashi, Y., et al. "A study on reliability improvement of the X-ray Computed Tomography." 2013. Retrieved from Internet (7 pp. including machine-generation English translation).

Industrial X-ray CT equipment measurement evaluation. 2012. Retrieved from Internet (7 pp. including machine-generated English translation).

Schlecht, J., et al. "Evaluating CT for Metrology: The Influence of Material Thickness on Measurements." National Institute of Standards and Technology. Oct. 7, 2014. Retrieved from Internet; 11 pages.

Office Action dated Aug. 4, 2020 in corresponding Japanese Application No. 2019-155611; 10 pages including English-language translation.

Shi et al., "Calibration of Industrial CT using two Forest-Balls", Ninth International Symposium on Precision Engineering Measurement and Instrumentation, Proc. of SPIE vol. 9446, Mar. 6, 2015, 8 pages.

Shi et al., "The Assessment of Industrial CT's Probing Error", Optical Metrology and Inspection for Industrial Applications III, Proc. of SPIE vol. 9276, Nov. 13, 2014, 10 pages.

* cited by examiner (a)

(b)

(a)

(b)

(a)

(b)

UTENSIL FOR EVALUATING LENGTH MEASUREMENT ERROR IN X-RAY CT DEVICE FOR THREE-DIMENSIONAL SHAPE MEASUREMENT

FIELD

The present invention relates to a utensil for evaluating a length measurement error in an X-ray CT device for three-dimensional shape measurement designed to measure the dimensions of a test object.

BACKGROUND

In recent years, the measurement of dimensions including those of the internal shape of a test object has been performed using an X-ray CT device developed as a device for observing the internal structure of a test object. Methods for evaluating the measurement accuracy of an X-ray CT device designed to measure a three-dimensional shape have been discussed in order to develop international standards; however, regarding current devices, for example, on the basis of measurement accuracy calculated in accordance with the Germany's domestic guideline VDI/VDE2630-1.3 (guideline on dimensional measurement by X-ray CT), accuracy assurance is provided for the devices. In addition, as a utensil for evaluating a length measurement error in an X-ray CT device for three-dimensional shape measurement (hereinafter referred to as a utensil) corresponding to VDI/VDE2630-1.3, a utensil made by Cael Zeiss Inc. is known (see Non-Patent Literature 1).

The utensil described in Non-Patent Literature 1 is one of a type referred to as a forest gauge. In the utensil referred to as the forest gauge, spheres are arranged in a space by installing upright support rods supporting the spheres on a stepwise base. One having 27 spheres and one having 22 spheres as the number of spheres are known.

Also, Patent Literature 1 proposes a calibrator of an X-ray CT device, which intends to accurately calibrate the dimensions of shapes including the internal shape of a test object from projection images obtained by the X-ray CT device. In a utensil described in Patent Literature 1, spheres are arranged in a space by firmly fixing the spheres on the outer circumference of a cylindrical body.

Before X-ray CT imaging of such a utensil, the coordinates of the respective spheres are measured by CMM (coordinate measuring machine: contact type three-dimensional coordinate measuring machine) or the like. In addition, from the difference between the value of an actual inter-sphere distance obtained by a coordinate measurement result and the value of an inter-sphere distance in an imaging space measured at the time of the X-ray CT imaging, a length measurement error by X-ray CT is evaluated.

CITATION LIST

Patent Literature

Patent Literature 1
Japanese Unexamined Patent Publication JP-A2014-190933

Non-Patent Literature

Non-Patent Literature 1
D. Weiss, R. Lonardoni, A. Deffner, C. Kuhn, Geometric image distortion in flat-panel X-ray detectors and its influence on the accuracy of CT-based dimensional measurements, 4th Conference on Industrial Computed Tomography (iCT), 19-21 Sep. 2012, Wels, Austria (iCT 2012)

SUMMARY

The calibrator described in Patent Literature 1 has the problem of being able to evaluate only a cylindrical region in an imaging space because no sphere can be arranged in the cavity inside the cylindrical body. On the other hand, in the utensil referred to as the forest gauge, it is possible to arrange spheres on the central axis; however, there is the following problem.

FIG. 15 is a schematic diagram illustrating an evaluation range in an imaging visual space when performing X-ray CT imaging on a conventional forest gauge. In addition, FIG. 15 illustrates the case where the 27-sphere forest gauge made by Carl Zeiss, Inc. is targeted for the X-ray CT imaging. In FIG. 15(a), the imaging visual space of a cylindrical shape is indicated by virtual lines, and in FIG. 15(b), an evaluation range at one time of X-ray CT imaging is illustrated. Also, FIG. 15(c) schematically illustrates evaluation ranges and unevaluable ranges in the imaging visual space when the X-ray CT imaging was performed three times at switched Z positions, and FIG. 15(d) is a diagram illustrating the mutual positional relationship among three conical spaces in the imaging visual space when the X-ray CT imaging was performed three times at the switched Z positions.

In a measurement space (X, Y, Z) specific to an X-ray CT device, the following distortion occurs. Firstly, a length reference in the X axial direction and a length reference in the Y axial direction are different, and for example, a perfect circle is deformed into an ellipse on a cross-sectional image orthogonal to the Z axis. Secondly, the length reference in the X axial direction and the length reference in the Y axial direction are gradually changed depending on the position of the Z axis, and thereby for example, a cylindrical shape is deformed into a truncated conical shape. Thirdly, local deformation occurs around a specific point. Fourthly, depending on the intersecting position of the X-Y plane with the Z axis, the X-Y plane is gradually rotated and twist-like deformation occurs in the space.

In a utensil like the forest gauge, spheres are arranged on a conical surface with the central sphere as the apex, and therefore a conical space as illustrated in FIG. 15(b) serves as an evaluation range where comparison with the value of an inter-sphere distance obtained from a coordinate measurement result by CMM is possible. For this reason, among the above-described first to fourth types of spatial distortion specific to an X-ray CT device, the second to fourth types of spatial distortion are difficult to capture.

Also, in the 27-sphere forest gauge made by Carl Zeiss Inc., the support rods supporting the spheres are installed upright on the base provided with steps, and a range where the shadow of the base part is imaged at the time of X-ray CT imaging is widened. In addition, only a space above the top step serves as an evaluation range (see FIG. 15(b)). For this reason, as compared with an evaluation range on the X-Y plane, an evaluation range in the Z axial direction in measurement by one time of X-ray CT imaging is narrowed. For example, in three times of X-ray CT imaging, as indicated by hatching in FIG. 15(c), the unevaluable ranges remain between the conical spaces. In order to eliminate such unevaluable ranges, it is necessary to measure an inter-sphere distance by repeatedly performing X-ray CT imaging while finely changing the position of a utensil in the Z axial direction many times within a height range corresponding to the longitudinal direction of the light receiving area of an X-ray detector. That is, it takes time to evaluate the measurement accuracy of an X-ray CT device.

Further, in the 27-sphere forest gauge made by Carl Zeiss Inc., since the spheres are arranged on a conical surface, the Z axis is aligned only with the sphere at the apex of the conical space, and therefore the mutual positional relationship among conical spaces each serving as an evaluation target at one time of X-ray CT imaging among multiple times of repeated X-ray CT imaging cannot be evaluated. Accordingly, as illustrated in FIG. 15(d), the deformation of the conical spaces can be captured, but the mutual positional relationship of a conical space at each time of X-ray CT imaging cannot be captured.

The present invention has been made in order to solve the above-described problems, and a first object is to provide a utensil for evaluating a length measurement error in an X-ray CT device for three-dimensional shape measurement, which makes it possible to sufficiently capture spatial distortion specific to the X-ray CT device and evaluate the three-dimensional shape measurement accuracy of the X-ray CT device.

FIG. 16 is a schematic diagram illustrating conventional methods for fixing a support rod supporting a sphere to a base. In a conventional forest gauge, when arranging spheres in a space by installing upright support rods supporting the spheres to a base, as a method for fixing the support rods, a method referred to as so-called split clamping has been employed. In FIG. 16(a), a fixing member 140 formed with a hole insertable with a support rod 136 is attached to a base 131 by screwing, and by operating a clamping screw 145 to narrow a clearance 144 in a split part, clamping force is given to the support rod 136 to fix the support rod 136 to the base 131. Also, in FIG. 16(b), a support rod 136 is fixed to a base 231 by using a fixing member 150 provided with a hole to be inserted with the support rod 136 and a male screw part 153, and screwing the male screw part 153 into a screw hole (female screw) formed in a base 231 in a state where the support rod 136 is bonded and fixed into the hole.

In a utensil where a sphere 35 is arranged by a conventional fixing method illustrated in FIG. 16, when bringing a probe of CMM into contact with the sphere for coordinate measurement, the position of the sphere 35 has been slightly changed in some cases because of the insufficiency of the rigidity and strength of the fixing member 140, 150. Also, when tilting the utensil or turning it upside down at the time of moving the utensil, the position of the sphere 35 has been slightly changed in some cases because of the insufficiency of clamping force by split clamping in FIG. 16(a), because of the engagement backlash of the screw in FIG. 16(b), or the like. The utensil for evaluating a length measurement error in the X-ray CT device for three-dimensional shape measurement is one for evaluating a length measurement error by X-ray CT from the difference between the value of an actual inter-sphere distance obtained from a coordinate measurement result and the value of an inter-sphere distance in an imaging space measured at the time of X-ray CT imaging, and therefore a change in sphere position after measuring the positions of respective spheres in the utensil by CMM is not allowed even if it is slight.

The present invention has been made in order to solve the above-described problem, and a second object is to provide a utensil for evaluating a length measurement error in an X-ray CT device for three-dimensional shape measurement, which prevents a sphere position from being changed even when a significant amount of external force is applied to a sphere or a support rod by contact of a probe or the like, or even when tilted or turned upside down at the time of movement.

FIG. 17 is a schematic cross-sectional view illustrating conventional bonding structures of a sphere at the tip of a support rod.

In a conventional forest gauge, when arranging spheres in a space, the support of spheres by the support rods is achieved by bonding ruby spheres or sapphire spheres commercially available as probes for CMM to the tips of the support rods. Bonding structures of a sphere to a support rod include one in which as illustrated in FIG. 17(a), the upper surface of a support rod 136 side is processed in a concave shape so as to fit to a spherical shape, and a sphere 35 is bonded in such a manner as to place the sphere 35 on the concave part. Also, as illustrated in FIG. 17(b), there is one in which a perforated sphere 235 applied with hole drilling is prepared, the tip of a support rod is provided with a thin shaft 239 corresponding to the hole, and the thin shaft 239 on the support rod 236 side is press-fitted into the hole of the perforated sphere 235 and then bonded and fixed. It is considered ideal that the clearance between the processed surface of the concave part and the lower surface of the sphere 35 illustrated in FIG. 17(a), or between the side surface of the thin shaft 239 and the inner wall surface of the hole of the perforated sphere 235 illustrated in FIG. 17(b) is uniform, and the clearance is filled with bond for fixation.

The bonding structure in FIG. 17(a) has the problem that it is difficult to smoothly and accurately process the processed surface of the concave part on the support rod 136 side so as to fit to the curved surface of the sphere 35, and the mutual positional relationship between the sphere 35 and the contact surface of the support rod 136 is unstable because of the unevenness of the processed surface of the concave part. Also, when the curvature radius of the processed surface of the concave part on the support rod 136 side is larger than the radius of the sphere, the sphere 35 rolls in the concave part of the support rod 136, and contrary when the curvature radius of the processed surface of the concave part is smaller than the radius of the sphere 35, the sphere 35 contacts with the support rod 136 at multiple partial points, such as contacting with parts inside the concave part and the edge of the concave part. For this reason, even when the same length of support rod 136 is made to support the sphere, the height position of the sphere is slightly different.

Further, in the bonding structure in FIG. 17(b), the thin shaft 239 made of a different material from the perforated sphere 235 is present inside the sphere. For this reason, there is a problem that a transmission image obtained by X-ray irradiation is disturbed. That is, non-negligible deviations occur between the central position of the X-ray CT image of the sphere itself and the shape of the sphere supposed to be detected, and the central position of the X-ray CT image of the sphere itself and the shape of the sphere obtained by actual X-ray irradiation.

The present invention has been made in order to solve the above-described problems, and a third object is to provide a utensil for evaluating a length measurement error in an X-ray CT device for three-dimensional shape measurement, which enables the positional relationships between respective multiple support rods and spheres supported by them to be made uniform.

Solution to Problem

A first aspect of the present invention includes: a base; multiple spheres arranged in an XYZ space on the base; and multiple support rods supporting each of the multiple spheres and installed upright on the base, in which in the XYZ space on the base, multiple spheres having different Z positions are arranged, and among the multiple spheres, one or more spheres are arranged in a vicinity of a Z axis, and in each of multiple X-Y planes having different Z positions, multiple outer circumference side spheres are arranged along one outer circumference.

A second aspect of the present invention is such that in the utensil for evaluating a length measurement error in an X-ray CT device for three-dimensional shape measurement according to the first aspect, outer circumference side spheres arranged in each of the multiple X-Y planes are cylindrically arranged.

A third aspect of the present invention is such that in the utensil for evaluating a length measurement error in an X-ray CT device for three-dimensional shape measurement according to the first or second aspect, the spheres arranged in the vicinity of the Z axis are multiple inner circumference side spheres.

A fourth aspect of the present invention is such that in the utensil for evaluating a length measurement error in an X-ray CT device for three-dimensional shape measurement according to any of the first to third aspects, in each of the multiple X-Y planes, multiple outer circumference side spheres and one or more inner circumference side spheres are arranged.

A fifth aspect of the present invention is such that in the utensil for evaluating a length measurement error in an X-ray CT device for three-dimensional shape measurement according to the third or fourth aspect, a distance between the inner circumference side spheres and the Z axis is set to be 20% or less of a distance between the outer circumference side spheres and the Z axis.

A sixth aspect of the present invention is such that in the utensil for evaluating a length measurement error in an X-ray CT device for three-dimensional shape measurement according to any of the first to fifth aspects, an arrangement range of the multiple spheres is a range where a distance in a Z direction between an X-Y plane having a lowest Z position and an X-Y plane having a highest Z position among the multiple X-Y planes is larger than a distance from the Z axis in XY directions.

A seventh aspect of the present invention is such that in the utensil for evaluating a length measurement error in an X-ray CT device for three-dimensional shape measurement according to any of the first to sixth aspects, the outer circumference side spheres are arranged in such a manner that an average value of the distances between respective outer circumference side sphere in each of the X-Y planes and the Z axis is equal amount the multiple X-Y planes.

An eighth aspect of the present invention is such that in the utensil for evaluating a length measurement error in an X-ray CT device for three-dimensional shape measurement according to any of the first to seventh aspects, the multiple X-Y planes are at least three X-Y planes whose mutual distances in a Z direction are equally separated.

A ninth aspect of the present invention is such that in the utensil for evaluating a length measurement error in an X-ray CT device for three-dimensional shape measurement according to any of the first to eighth aspects, as the arrangement of the outer circumference side spheres, multiple sets of two spheres separated from the Z axis by a predetermined distance and oppositely arranged with respect to the Z axis are arranged in each of the multiple X-Y planes having different Z positions, and thereby at least four are arranged in each of the X-Y planes.

A tenth aspect of the present invention is such that in the utensil for evaluating a length measurement error in an X-ray CT device for three-dimensional shape measurement according to the ninth aspect, the multiple X-Y planes are at least three X-Y planes whose mutual distances in a Z direction are equally separated, and among the multiple spheres, multiple sets of two spheres oppositely arranged with respect to the Z axis are arranged, and thereby spheres arranged in each of the three X-Y planes are equally arranged at intervals of substantially 30 degrees on a circle around the Z axis in a plan view where the three X-Y planes are superposed.

An eleventh aspect of the present invention is such that in the utensil for evaluating a length measurement error in an X-ray CT device for three-dimensional shape measurement according to the ninth or tenth aspect, in each of the multiple X-Y planes, one or more inner circumference side spheres are also arranged, and the one or more inner circumference side spheres are arranged on lines connecting the outer circumference side spheres that are oppositely arranged.

A twelfth aspect of the present invention is such that in the utensil for evaluating a length measurement error in an X-ray CT device for three-dimensional shape measurement according to any of the first to eleventh aspects, the outer circumference side spheres are arranged at regular intervals on a circle around the Z axis in a plan view of one X-Y plane.

A thirteenth aspect of the present invention is such that in the utensil for evaluating a length measurement error in an X-ray CT device for three-dimensional shape measurement according to any of the first to twelfth aspects, the base has a flat surface on a top thereof, and the lengths of the multiple support rods are different each other so that the Z positions of the arranged multiple spheres are different each other.

A fourteenth aspect of the present invention is such that in the utensil for evaluating a length measurement error in an X-ray CT device for three-dimensional shape measurement according to any of the first to thirteenth aspects, the multiple support rods are respectively provided with support rod holding mechanisms inserted into holes that are formed in the base so as to correspond to the number of the multiple support rods, and each of the support rod holding mechanisms includes: a bottomed cylindrical member that is inserted into one of the holes of the base, whose side surface is provided with multiple through-holes, and that is provided with a space into which a one of the support rods is inserted; a loading bolt whose central part is provided with a hole through which the support rod is made to penetrate and whose outer circumferential part is provided with a male screw part screwed into a female screw formed on the inner wall of an opening of the cylindrical member; fixing block inserted into one of the through-holes of the cylindrical member and having a convex part that abuts on the side surface of the support rod whose end part on a side opposite to a side where a sphere is supported abuts on the bottom of the cylindrical member, and a load transmitting block that is inserted into one of the through-holes of the cylindrical member and in two directions, transmits force generated when the loading bolt is fastened to the cylindrical member by screwing the female screw and the male screw part together, the two directions being a direction to constrain the degree of freedom of the support rod in a translation direction in an X-Y plane and a direction to constrain the degree of freedom of the support rod in a translation direction on the Z axis.

A fifteenth aspect of the present invention is such that in the utensil for evaluating a length measurement error in an X-ray CT device for three-dimensional shape measurement according to the fourteenth aspect, the through-holes of the cylindrical member are provided in three positions of the side surface of the cylindrical member at regular intervals around a cylinder axis, and in two of the through-holes, the fixing blocks are arranged, and in one, the load transmitting block is arranged.

A sixteenth aspect of the present invention is such that in the utensil for evaluating a length measurement error in an X-ray CT device for three-dimensional shape measurement according to the fourteenth or fifteenth aspect, the load transmitting block includes three wedge-shaped members mutually joined via a tilt surface.

A seventeenth aspect of the present invention is such that in the utensil for evaluating a length measurement error in an X-ray CT device for three-dimensional shape measurement according to any of the first to sixteenth aspects, one end of each of the support rods is provided with a conical concave part, and a sphere is supported in contact with the conical tilt surface of the conical concave part.

An eighteenth aspect of the present invention is such that in the utensil for evaluating a length measurement error in an X-ray CT device for three-dimensional shape measurement according to the seventeenth aspect, a bottom of the conical concave part of the support rod is provided with a through-hole.

Advantageous Effects of Invention

According to the first to eighteenth aspects of the present invention, since in the XYZ space on the base, one or more spheres are arranged in the vicinity of the Z axis, and in each of the multiple X-Y planes having different Z positions, multiple outer circumference side spheres are arranged along one outer circumference, not only from a region where the multiple outer circumference side spheres are arranged in the space, but also to a region where one or more spheres are arranged in the vicinity of the Z axis on the inner side of the region where the outer circumference side spheres are arranged, an imaging space can be evaluated. Also, since in each of the multiple X-Y planes having different Z positions, multiple outer circumference side spheres are arranged along one outer circumference, the problem that an unevaluable region remains between conical spaces as in a conventional forest gauge where spheres are arranged on conical surfaces can be solved.

According to the fourth aspect of the present invention, one or more inner circumference side spheres are arranged in each of the multiple X-Y planes, and thereby multiple spheres having different Z positions are arranged in the vicinity of the Z axis, so that multiple measurement points can be given in the Z direction at the center of an evaluation range. In doing so, the mutual positional relationship among cylindrical spaces each serving as an evaluation target at each time of X-ray CT imaging among multiple times of repeated X-ray CT imaging can be evaluated.

According to the sixth aspect of the present invention, since the arrangement range of the multiple spheres is set as a range where the distance in a Z direction between an X-Y plane having the lowest Z position and an X-Y plane having the highest Z position among the multiple X-Y planes is larger than a distance from the Z axis in XY directions, a cylindrical imaging visual space can be isotropically evaluated by a smaller number of times of X-ray CT imaging than before. The number of times of performing repeated measurement with a Z axis position changed can be reduced than before, and therefore imaging time for evaluating the measurement accuracy of an X-ray CT device can be shortened.

According to the ninth aspect of the present invention, since as the arrangement of the outer circumference side spheres, at least four spheres are arranged separated from the Z axis by a predetermined distance in each of the multiple X-Y planes having different Z positions, a conventional structure where spheres are arranged on conical surfaces is not formed, and therefore spatial distortion specific to an X-ray CT device can be sufficiently captured. Accordingly, the three-dimensional shape measurement accuracy of the X-ray CT device can be evaluated.

According to the thirteenth aspect of the present invention, since by forming the top of the base as a flat surface and differentiating the lengths of the multiple support rods, the arrangement of the spheres having different Z positions is achieved, the shadow of a step appearing when a base is formed stepwise as conventional is not imaged, and a range evaluable at one time of imaging is widened, thus making it possible to reduce the number of times of performing repeated measurement with a Z axis position changed than before.

According to the fourteenth to eighteenth aspects of the present invention, since each support rod can be constrained in the three-dimensional space by the support rod holding mechanism, a utensil that even when a significant amount of stress is applied to a sphere or a support rod, or even when turned upside-down during transportation or installation, prevents a change in sphere position can be fabricated.

According to the seventeenth and eighteenth aspects of the present invention, since in a support rod, the tip supporting a sphere is shaped as the conical concave part, the sphere comes into line contact with the conical tilt surface of the conical concave part, and individual differences among spheres can be made less influential to uniform the positional relationships between spheres and corresponding support rods.

According to the eighteenth aspect of the present invention, by providing the bottom of the conical concave part of the support rod with the through-hole, bond can be allowed to escape, and force for further pulling the sphere toward the support rod side is generated when the bond cures, making it possible to increase force for holding the sphere.

DETAILED DESCRIPTION

Description of Embodiments

Figure 1:
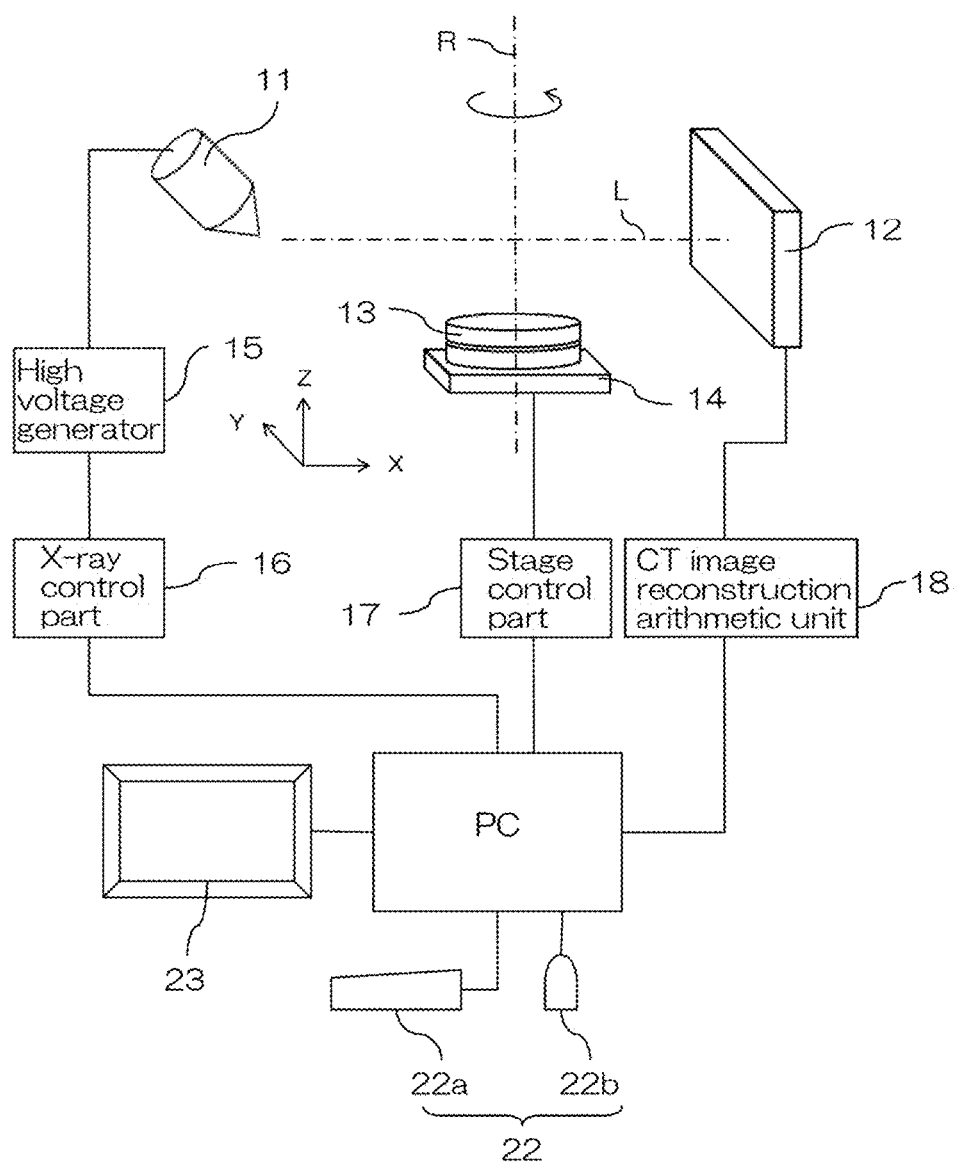
FIG. 1 is a schematic diagram of an X-ray CT device for three-dimensional shape measurement.

In the following, an embodiment of the present invention will be described on the basis of drawings. FIG. 1 is a schematic diagram of an X-ray CT device for three-dimensional shape measurement.

The X-ray CT device for three-dimensional shape measurement (hereinafter referred to as an X-ray CT device) includes an X-ray irradiation part 11, an X-ray detector 12, and a rotation stage 13. The X-ray CT device is one that performs non-destructive internal observation and three-dimensional shape measurement with a test object placed on the rotation stage 13 disposed between the oppositely arranged X-ray irradiation part 11 and X-ray detector 12.

The X-ray irradiation part 11 is provided inside with an X-ray tube as an X-ray source, and from the X-ray tube, generates X-rays corresponding to tube voltage and tube current supplied from a high voltage generator 15. The high voltage generator 15 is controlled by an X-ray control part 16, and the X-ray control part 16 is connected to a personal computer PC installed with control software for controlling the whole of the X-ray CT device. The X-ray detector 12 is one in which an image intensifier (I.I.) is combined with a CCD camera, or an FPD (Flat Panel Detector), and connected to the personal computer PC via a CT image reconstruction arithmetic unit 18. In addition, the X-ray detector 12 is configured to be separable/approachable with respect to the rotation stage 13 in order to scale a fluoroscopic imaging region. Further, the rotation stage 13 is also separable/approachable with respect to the X-ray irradiation part 11.

The rotation stage 13 is adapted to rotate with a Z-axis orthogonal to an X-axis along an X-ray light axis L connecting from the X-ray irradiation part 11 to the X-ray detector 12 as a rotation axis R, and also be movable in the horizontal direction corresponding to XY directions and the vertical direction corresponding to a Z direction by a stage driving mechanism 14. In addition, the stage driving mechanism 14 is connected to the personal computer PC via a stage control part 17.

When performing X-ray CT imaging, rotation is given to the rotation stage 13 around the rotation axis R while irradiating the test object placed on the rotation stage with X-rays from the X-ray irradiation part 11. Then, transmitted X-rays from all directions over 360 degrees around the test object are detected by the X-ray detector 12, and the resulting X-ray transmission data is retrieved into the CT image reconstruction arithmetic unit 18.

The CT image reconstruction arithmetic unit 18 includes a computer including: a ROM, RAM, hard disk, and the like as storage devices for storing programs, detection data from the X-ray detector 12, and the like; and a CPU as an arithmetic unit. In the CT image reconstruction arithmetic unit 18, the retrieved X-ray transmission data covering the 360 degrees is used to construct a tomographic image (CT image) of the test object, which is sliced along a plane parallel with the X-Y plane. The CT image is transmitted from the CT image reconstruction arithmetic unit 18 to the personal computer PC, and used for three-dimensional imaging by a three-dimensional image construction program installed in the personal computer PC.

The personal computer PC is connected with a display device 23 such as a liquid crystal display and input devices 22 including a keyboard 22a and a mouse 22b. In addition, the keyboard 22a and the mouse 22b are ones for providing inputs by an operator in various operations. The display device 23 displays a CT image transmitted from the CT image reconstruction arithmetic unit 18 to the personal computer PC, as well as displays a three-dimensional image constructed using the CT image. In addition, the functions of the CT image reconstruction arithmetic unit 18 may be integrated with the personal computer PC and implemented as computer's peripheral devices and software by one computer.

Next, the utensil 30 for evaluating a length measurement error used when evaluating the X-ray CT device as one for three-dimensional shape measurement will be described. The X-ray CT device obtains volume data referred to as a reconstruction image from multiple projection images detected by the X-ray detector 12, and therefore when evaluated as one for three-dimensional shape measurement, is required to be able to confirm length measurement accuracy over a wide range relative to the X-ray detection region of the X-ray detector 12. Also, the X-ray CT device changes the positional relationship among the X-ray source, the rotation stage 13, and the X-ray detector 12 in order to change the magnification ratio of a projection image, and is therefore required to be able to evaluate a geometric error due to displacement from a state where respective components are ideally assembled. Further, the X-ray CT device performs X-ray imaging with the rotation stage 13 rotated, and is therefore also required to be able to evaluate the motion error of the rotation stage 13.

Figure 2:
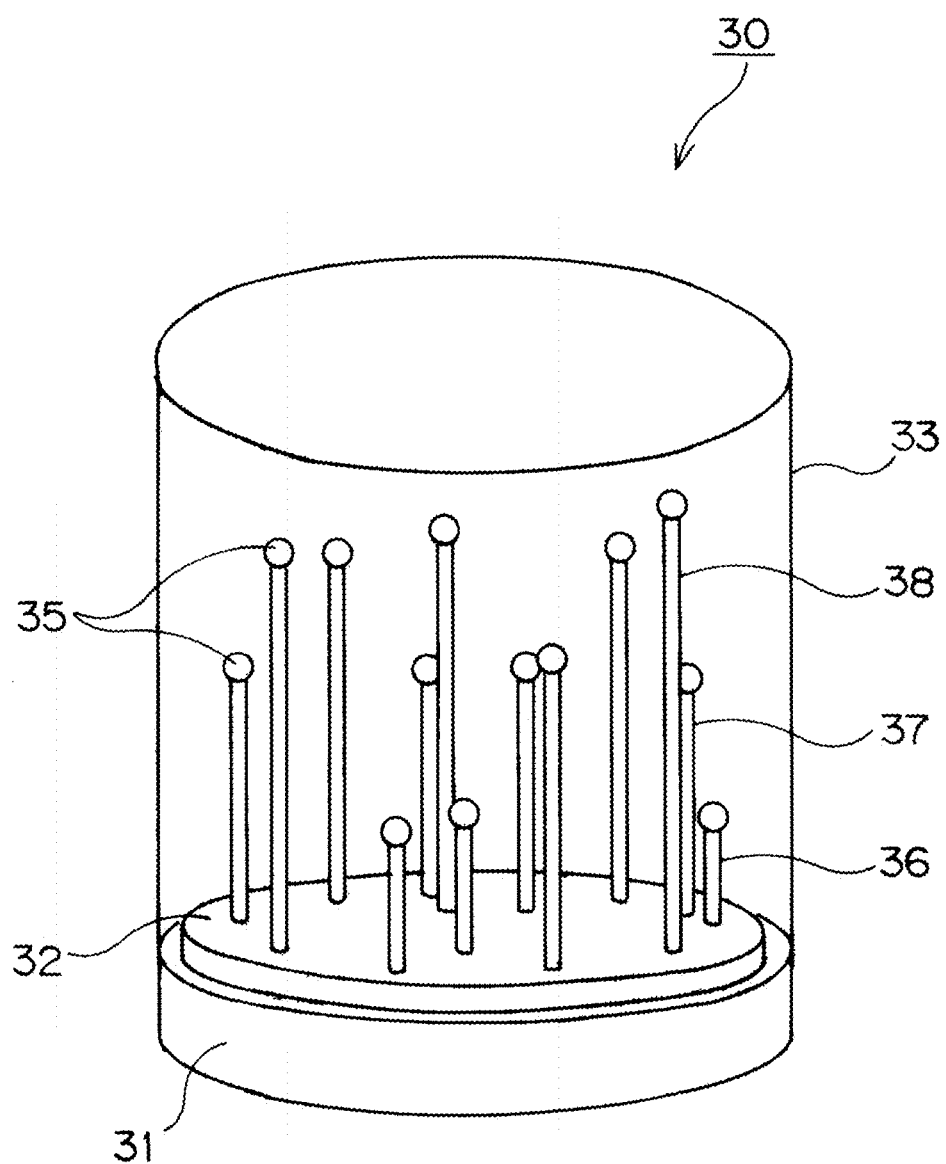
FIG. 2 is a perspective view of a utensil 30 for evaluating a length measurement error in the X-ray CT device for three-dimensional shape measurement according to the present invention.

FIG. 2 is a perspective view of the utensil 30 for evaluating a length measurement error in the X-ray CT device for three-dimensional shape measurement according to the present invention.

The utensil 30 for evaluating a length measurement error in the X-ray CT device for three-dimensional measurement (hereinafter referred to as a utensil 30) is such that support rods 36, 37, 38 whose tips are fixed with spheres 35 and whose lengths are different are attached to a base 31, and thereby 15 spheres 35 are arranged in an XYZ space on the base 31. On a flat surface 32 on the top of the base 31, the support rods 36, 37, 38 supporting the spheres 35 and having different lengths are installed upright at predetermined intervals. The base 31 is formed of a low thermal expansion metallic material whose thermal deformation is extremely small. Also, as the spheres 35, spherical bodies whose shape error is small (sphericity is high) are employed, and for the support rods 36, 37, 38, a material such as ceramic is employed.

The arrangement space of the sphere 35 on the top of the base 31 is adapted to be covered with a cylindrical cover 33 at the time of storage and at the time of use so as to prevent the spatial arrangement of the respective spheres 35 after coordinate measurement by CMM from being disordered. The cover 33 is formed of a material having relatively high X-ray transmittance, such as an acrylic resin. In addition, the cover 33 is not required to be transparent to visible light, but is desirably transparent to visible light. When it is transparent, an operator can directly view the inside, and therefore structural understanding can be facilitated.

The support rods 37 has a dimension longer than the support rods 36 by 30 mm, and the support rods 38 has a dimension longer than the support rods 37 by 30 mm. Using the support rods 36, 37, 38 whose lengths are different from each other by 30 mm enables the multiple spheres 35 to be arranged at three Z positions (e.g., five per one Z position). That is, by differentiating the lengths of the support rods 36, 37, 38 used to support the spheres 35 in the three-step manner, the sphere 35 are arranged in three X-Y planes having different Z positions. In addition, in the present embodiment, by setting the difference in length between the shortest support rods 36 and the intermediate-length support rods 37 and the difference in length between the intermediate-length support rods 37 and the longest support rods 38 to have the same length, the intervals between the three Z positions are equalized.

Figure 3:
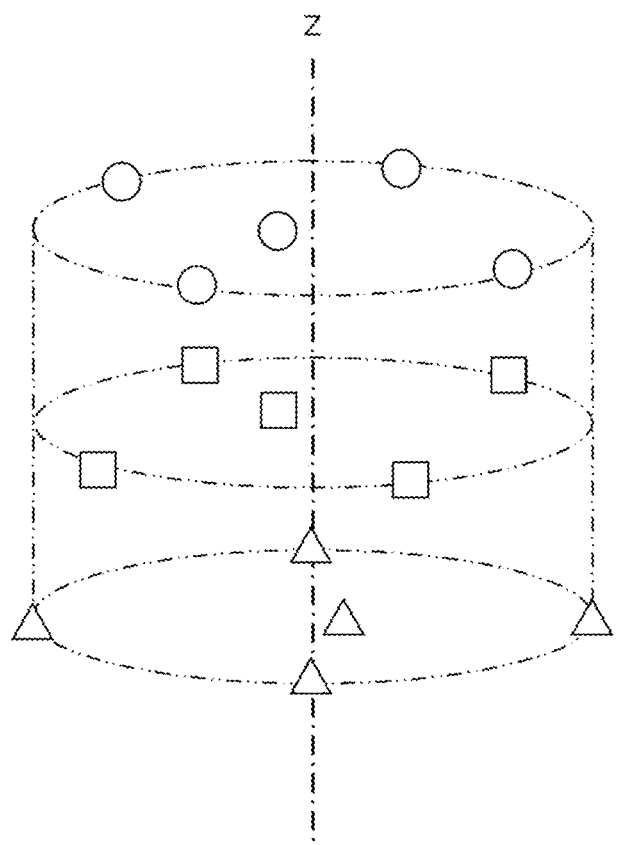
FIG. 3 is a schematic diagram illustrating the arrangement of spheres 35.
Figure 4:
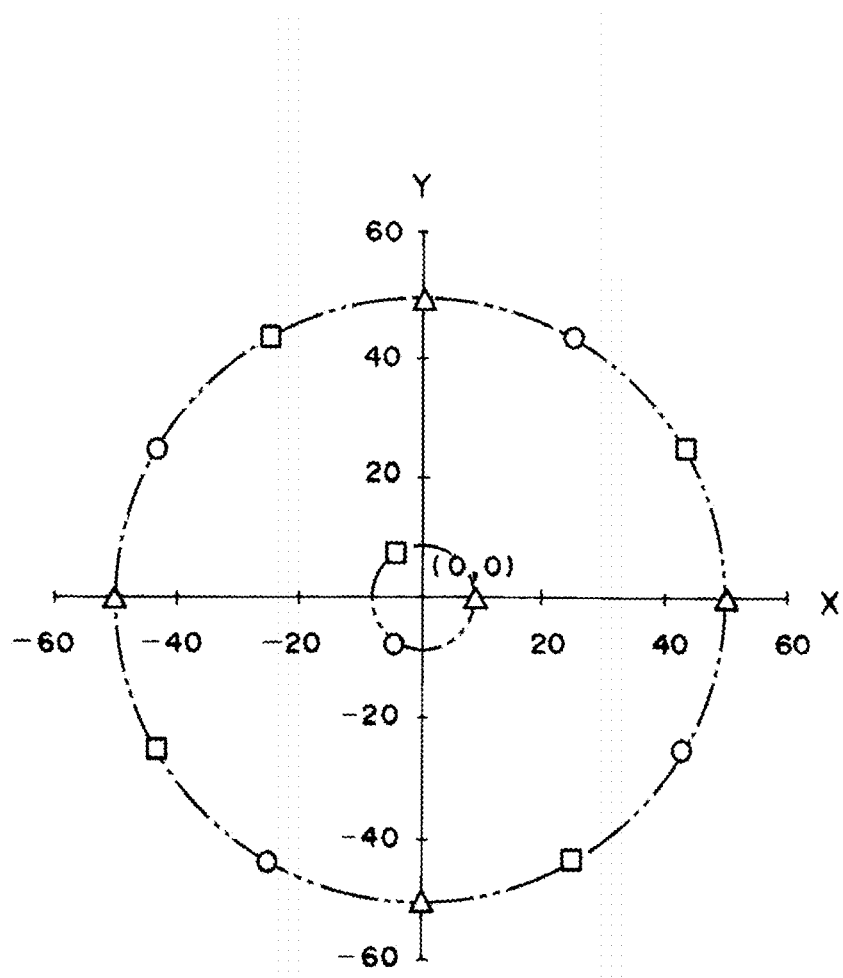
FIG. 4 is a schematic diagram illustrating the arrangement of the spheres 35.

FIG. 3 and FIG. 4 are schematic diagrams illustrating the arrangement of the spheres 35. FIG. 3 is a three-dimensional image illustrating the arrangement of the respective spheres 35 in a cylindrical imaging space indicated by dashed-two dotted lines, and FIG. 4 is a schematic plan view. In FIG. 4, projection coordinates (Xi, Yi) obtained by projecting the positions of the respective spheres 35 parallel to the Z axis toward the X-Y plane at the Z position of the spheres 35 supported by the shortest support rods 36 are illustrated. Here, triangles (Δ) in the view represent the positions of the five spheres 35 supported by the shortest support rods 36, quadrangles (□) represent the positions of the five spheres 35 supported by the intermediate-length support rods 37, and circles (○) represent the positions of the five spheres 35 supported by the longest support rods 38.

As illustrated in FIG. 3 and FIG. 4, in this utensil 30, on a circle (inner circle) having a radius of approximately 10 mm around the origin (0, 0) of the projection coordinates, one sphere 35 at each of the three Z positions is arranged, and on a circle (outer circle) having a radius of approximately 50 mm, four spheres 35 at each of the three Z positions are arranged displaced from each other by approximately 90 degrees in a substantially cross shape to thereby arrange the 12 spheres 35 in total. Since the origin (0, 0) of the projection coordinates also corresponds to the Z axis, in each of the three X-Y planes having different Z positions, five spheres are arranged, i.e., the 15 spheres in total are arranged in total. Since the differences in length between the respective support rods 36, 37, 38 are the same length such as 30 mm, the three X-Y planes are equally mutually separated in terms of distance in the Z direction. In addition, in one X-Y plane, the arrangement of spheres arranged at positions away from a sphere arranged on the inner circle in the vicinity of the Z axis and on the outer circle separated from the Z axis by the predetermined distance is such that by arranging multiple sets of two spheres oppositely arranged with respect to the Z axis, i.e., in the present embodiment, by arranging the two sets of two spheres oppositely arranged with respect to the Z axis, four spheres 35 are arranged. Further, by adjusting the positions of the two sets so that two line segments each connecting between two spheres on the same line passing through the Z axis have an orthogonal relationship, the arrangement of the four spheres 35 is made substantially cross-shaped, in which the four spheres 35 are displaced from each other by approximately 90 degrees.

In the three different X-Y planes, the positional relationship among the respective spheres 35 arranged on the outer circle is such that in the plan view as illustrated in FIG. 4, the spheres 35 are arranged on the same circle around the Z axis at regular intervals. That is, positions on the circle around the origin (0, 0) in FIG. 4 are positions separated from each other by substantially 30 degrees. In the present embodiment, with the arrangement of the four spheres 35 indicated by the triangles (Δ) in the X-Y plane at the lowest Z position as a reference, the four spheres 35 indicated by the quadrangles (□) in the X-Y plane whose X position is displaced upward are arranged at positions rotated anticlockwise by substantially 30 degrees around the Z axis, and the four spheres 35 indicated by the circles (○) in the X-Y plane whose Z position is further displaced upward from the previous one are arranged at positions rotated anticlockwise by substantially 30 degrees around the Z axis. That is, on the outer circumferential surface of the cylinder having a radius of 50 mm and a height of 60 mm, the spheres 35 are spirally arranged at every 90 degrees in the order of the triangle (Δ), the quadrangle (□), and the circle (○) on the basis of the combination of the 30-degree rotation with the Z axis as a rotation axis and the 30-mm translation parallel to the Z axis. The multiple outer circumference side spheres arranged in the respective three X-Y planes are cylindrically arranged as evaluation points in the cylindrically-shaped region (indicated by the dashed-two dotted lines) of the imaging space. In addition, the multiple outer circumference side spheres are equally arranged at intervals of substantially 30 degrees on the circle around the Z axis in a plan view by rotating and arranging the arrangement positions of four spheres arranged in each of the three X-Y planes by substantially 30 degrees around the Z axis with respect to the arrangement positions of spheres in an adjacent X-Y plane.

Four among the five spheres 35 supported by the shortest support rods 36, four among the five spheres 35 supported by the intermediate-length support rods 37, and four among the five spheres 35 supported by the longest support rods 38 are equally arranged on the circle having a radius of 50 mm around the origin (0, 0) of the projection coordinates as described above. In the present embodiment, by arranging four spheres 35 in each of the X-Y planes on the same circle as described, the distances between the respective spheres 35 and the Z axis are equalized. In addition, as long as among the respective spheres 35 excluding the three spheres 35 in the vicinity of the Z axis illustrated in FIG. 4, the average value of the distances between the origin (0, 0) and the respective triangles (Δ), the average value of the distances between the origin (0, 0) and the respective quadrangles (□), and the average value of the distances between the origin (0, 0) and the respective circles (○) are equalized, the spheres 35 are not necessarily required to be arranged on the same circle. That is, regarding the spheres 35 arranged in the respective X-Y planes other than the three in the vicinity of the Z axis, the X-Y plane-based average values of the distances between the respective spheres 35 and the Z axis are only required to be roughly equalized.

One among the five spheres 35 supported by the shortest support rods 36, one among the five spheres 35 supported by the intermediate-length support rods 37, and one among the five spheres 35 supported by the longest support rods 38 are inner circumference side spheres of the present invention and arranged at equal intervals on the circle having a radius of approximately 10 mm or less in the vicinity of the Z axis. That is, on a substantially straight line in the Z direction, one sphere 35 is arranged at each of the three types of Z positions. In addition, the utensil 30 is configured to support the spheres 35 respectively using the support rods 36, 37, 38, and therefore the three spheres 35 whose Z positions are only different cannot be strictly arranged on the origin (0, 0) of the projection coordinates. For this reason, in the present embodiment, by arranging at equal intervals on the circle having a radius of approximately 10 mm or less in the vicinity of the Z axis, the equal arrangement of the multiple spheres in the Z axis direction (the equal arrangement of the spheres in the longitudinal direction) is achieved. In addition, a guide for the vicinity of the Z axis is a distance range where a distance from the Z axis is approximately 20% or less of the diameter of the circle defining the arrangement positions of four spheres 35 in each of the X-Y planes. In the present embodiment, the three spheres 35 respectively supported by the support rods 36, 37, 38 having different lengths are arranged on the inner circumferential circle at equal intervals; however, as long as three sphere positions having different heights along the Z axis can be obtained, they are not required to be arranged on the same circle. The "vicinity" of the vicinity of the Z axis in the present invention includes being separated from the center by a distance enough to be regarded as a central position, and also includes being on the Z axis as the center. Further, by arranging a sphere 35 arranged in the vicinity of the Z axis on a line connecting two having a diagonal relationship interposing the origin (0, 0) among four spheres 35 arranged on the circle having a radius of 50 mm in each X-Y plane at a corresponding Z position, grasping a displacement amount from the Z axis and equal arrangement around the Z axis in a plan view are facilitated.

Figure 5:
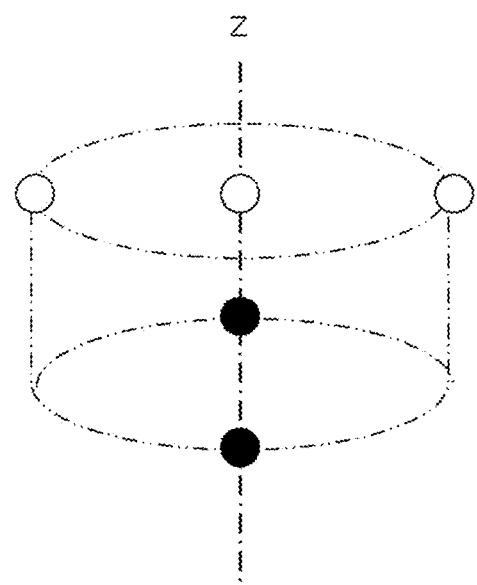
FIG. 5 is a schematic diagram illustrating a variation of the arrangement of the spheres 35.
Figure 6:
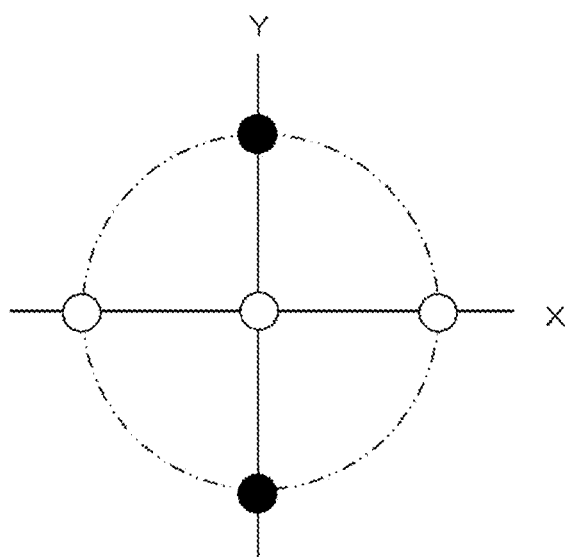
FIG. 6 is a schematic diagram illustrating the variation of the arrangement of the spheres 35.
Figure 7:
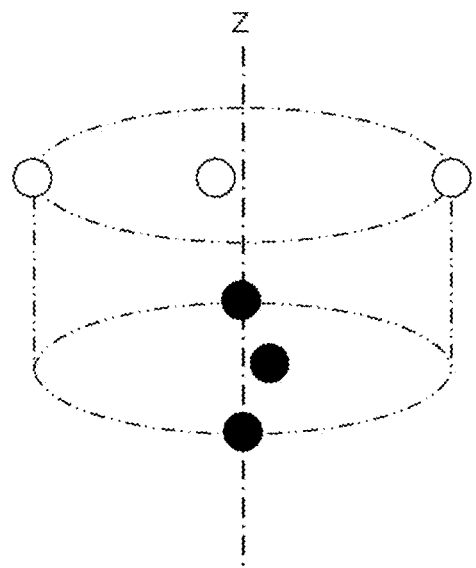
FIG. 7 is a schematic diagram illustrating a variation of the arrangement of the spheres 35.
Figure 8:
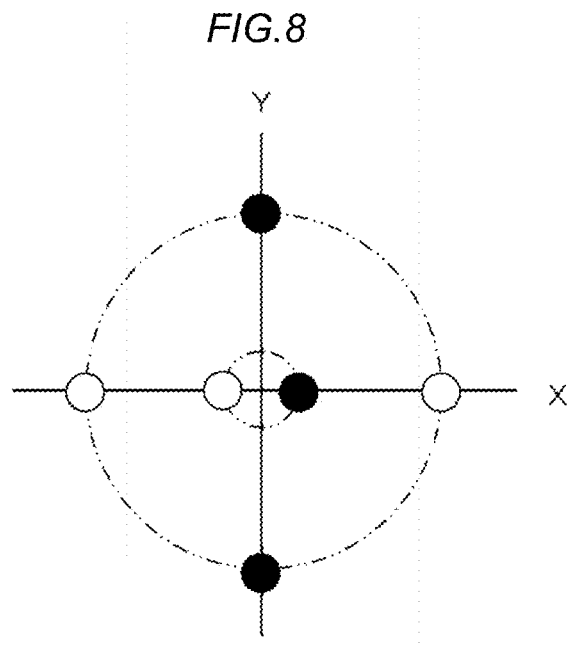
FIG. 8 is a schematic diagram illustrating the variation of the arrangement of the spheres 35.

FIG. 5 to FIG. 8 are schematic diagrams illustrating variations of the arrangement of spheres 35. FIG. 5 and FIG. 7 are three-dimensional images illustrating the arrangement of the respective spheres 35 in an imaging space, and FIG. 6 and FIG. 8 are schematic plan views. In the variations, the positions of spheres 35 in an X-Y plane having a low Z position are indicated by black circles, and the positions of spheres 35 in an X-Y plane having a high Z position are indicated by white circles.

In the arrangement of the spheres 35 illustrated in FIG. 5 and FIG. 6, arranging one sphere on the Z axis results in one evaluation point in the Z direction. In addition, two spheres 35 are arranged along one circumference around the Z axis in each of the two different X-Y planes. In the plan view illustrated in FIG. 6, respective spheres 35 are arranged on the same circle at regular intervals.

In the arrangement of the spheres 35 illustrated in FIG. 5 and FIG. 6, the one sphere 35 on the Z axis enables the imaging space to be evaluated in a region on the inner side of a region where the outer circumference side spheres are arranged. In addition, by oppositely arranging two spheres along an outer circumferential circle so as to be able to at least project the spheres 35 to positions near the maximum lateral X-ray detection region of the X-ray detector 12, multiple evaluation points can be obtained in the imaging space of a cylindrical shape. Also, by arranging two outer circumference side spheres 35 in each of the two X-Y planes having different Z positions, the spheres 35 can be projected to positions near the maximum longitudinal X-ray detection region of the X-ray detector 12 and to different height positions. For this reason, when performing imaging multiple times with a Z position changed, the inside of the cylindrical imaging visual space can be evaluated by a small number of imaging times without creating an unevaluable range between single imaging spaces. Further, by arranging two spheres 35 in each of the X-Y planes having different Z positions, the evaluation of the motion error of the rotation stage 13 and the evaluation of a geometric error can be performed.

Figure 15:
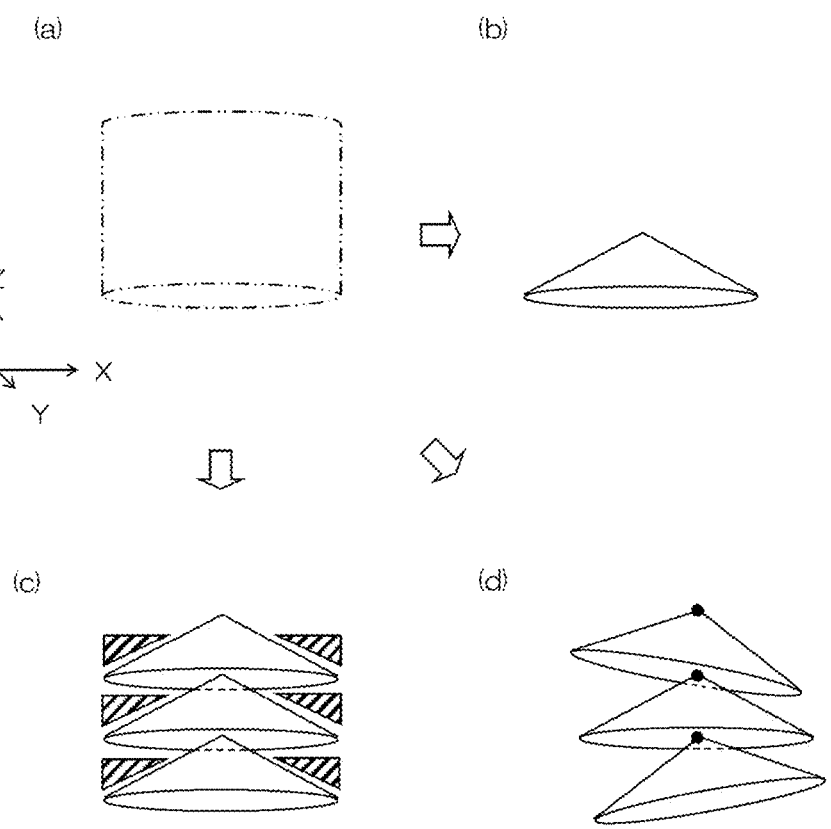
FIG. 15 is a schematic diagram illustrating an evaluation range in an imaging visual space when performing X-ray CT imaging on a conventional forest gauge.
Figure 16:
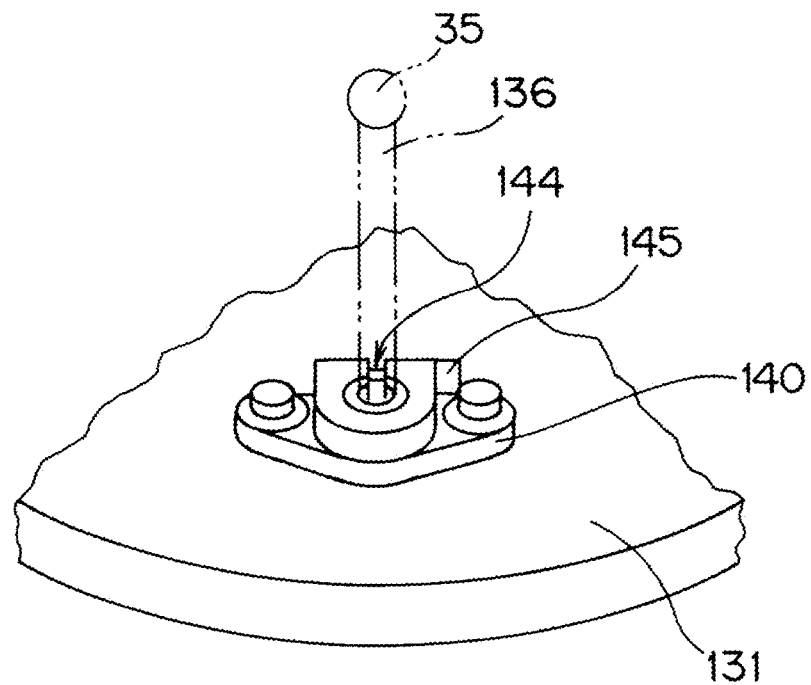
FIG. 16 is a schematic diagram illustrating conventional methods for fixing a support rod supporting a sphere to a base.
Figure 16:
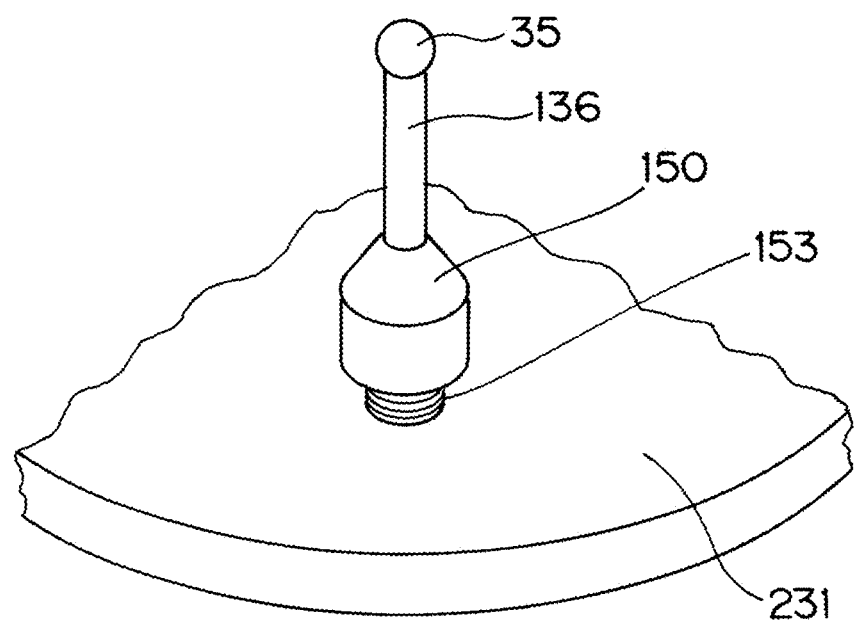

In addition, in this variation, in the two different X-Y planes, two spheres 35 are oppositely arranged in each of the X-Y planes; however, as long as respective spheres 35 in each of the two X-Y planes are arranged along one outer circumferential circle, it is not required to strictly arrange them at regular intervals, or oppositely arrange them in each of the X-Y planes. The "outer circumference" of the outer circumference side spheres in the present invention refers to a circumference such as a circle having a diameter or an ellipse having the major axis, which enables the spheres 35 to be projected to positions near the maximum lateral X-ray detection region of the X-ray detector 12. By arranging two or more spheres in each of two or more X-Y planes having different Z positions, the problem that spheres are arranged on conical surfaces as in the conventional forest gauge described with reference to FIG. 15(c), and thereby unevaluable ranges are created in a cylindrical imaging space is solved.

The outer circumference side spheres in the present invention refer to spheres arranged in multiple X-Y planes along outer circumferences enabling the spheres 35 to be projected to positions near the maximum lateral X-ray detection region of the X-ray detector 12, and on condition of lying along circumferences, all the spheres are not required to be in a relationship where distances from the Z axis are equal. Also, cylindrically arranging the outer circumference side spheres in the present invention refers to the arrangement of the spheres in a state where among different X-Y planes, translating multiple spheres in each X-Y plane toward another X-Y plane in parallel with the Z axis makes it possible to form a cylindrical shape whose height is the difference in Z position between the two X-Y planes.

In the arrangement of the spheres 35 illustrated in FIG. 7 and FIG. 8, there are two evaluation points in the Z direction. That is, one sphere 35 is arranged in the vicinity of the Z axis in each of the two X-Y planes, and the spheres 35 in the vicinity of the Z axis in the different X-Y planes have a positional relationship of lying along an inner circumferential circle in the vicinity of the Z axis in the plan view illustrated in FIG. 8. The "inner circumference" of the inner circumference side spheres in the preset invention refers to a circumference on the inner side with respect to the outer circumference, and by making the positional relationship of the spheres in the vicinity of the Z axis in the different X-Y planes have a certain design regularity, uniformity in fabricating the utensil can be ensured. As compared with the variation of FIG. 5 and FIG. 6, the evaluation points in the Z direction is increased in number, and thereby the mutual positional relationship among cylindrical spaces each serving as an evaluation target at each time of X-ray CT imaging among multiple times of repeated X-ray CT imaging can be evaluated.

The arrangement of spheres 35 can be modified in other ways than those described with reference to FIG. 1 to FIG. 8. That is, depending on the size of the X-ray detector 12 or the necessity of multiple times of X-ray CT imaging performed with a Z axis position changed, the number of X-Y planes in which multiple outer circumference side spheres are arranged, and the number of spheres arranged there can be changed.

Figure 9:
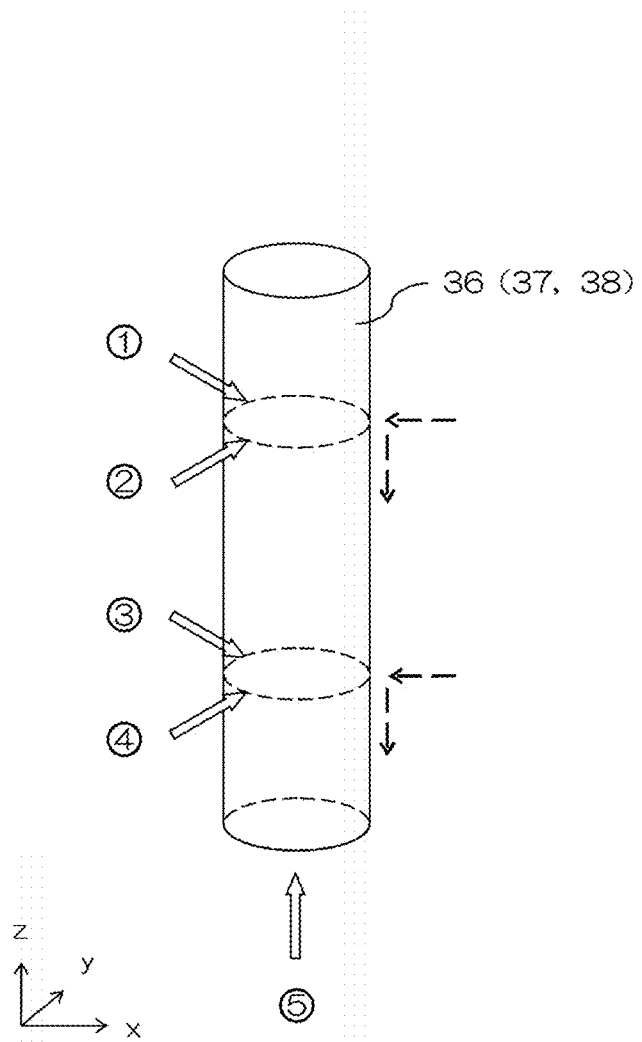
FIG. 9 is a diagram illustrating constraint conditions in a three-dimensional space at the time of fixing cylindrical support rods 36, 37, or 38 to a base 31.
Figure 10:
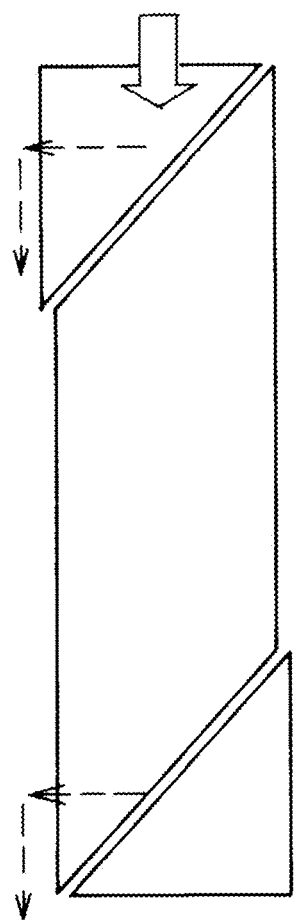
FIG. 10 is a diagram illustrating force transmission by wedge-shaped blocks.

A structure for fixing the support rods 36, 37, 38 supporting the spheres 35 to the base 31 will be described. FIG. 9 is a diagram illustrating constraint conditions in a three-dimensional space at the time of fixing the cylindrical support rod 36 to the base 31. FIG. 10 is a diagram illustrating force transmission by wedge-shaped blocks.

In order to fix the cylindrical support rods 36, 37, 38 to the base 31, five degrees of freedom indicated marked with circled signs 1 to 5 together with outlined arrows in FIG. 9 are taken into account. That is, in an X-Y plane, constraint is performed at points 1 and 2 in FIG. 9 by force from a direction opposite to them (force from a direction 180-degree opposite to the middle between 1 and 2), and constraint is performed at points 3 and 4 by force from a direction opposite to them (force from a direction 180-degree opposite to the middle between 3 and 4). Translation in the Z axis direction is constrained at a point 5 in FIG. 9 by force from a direction opposite to it. Further, rotation in the Z axis direction can be constrained by frictional force due to surface contact in addition to the constraint at the points 1 to 5 in FIG. 9.

In order to constrain the degree of freedom of the support rods 36, 37, 38 in the translation direction in the X-Y plane and the degree of freedom in the translation direction (vertical direction) on the Z axis, it is necessary to simultaneously apply bidirectional forces whose directions are different by 90 degrees as indicated by dashed line arrows in FIG. 9 to the support rod 36. As a mechanism enabling such force transmission, a wedge-shaped block in which a block shape for constraining the support rod 36 is combined with a wedge shape having an acute angle of 45 degrees can be employed. As illustrated in FIG. 10, in the wedge-shaped block in which three wedge-shaped members contacting with each other via a tilt surface are combined, from a load indicated by an outlined arrow bidirectional forces whose directions are different by 90 degrees as indicated by dashed line arrows in FIG. 10 can be generated by action of tilt surfaces.

Figure 11:
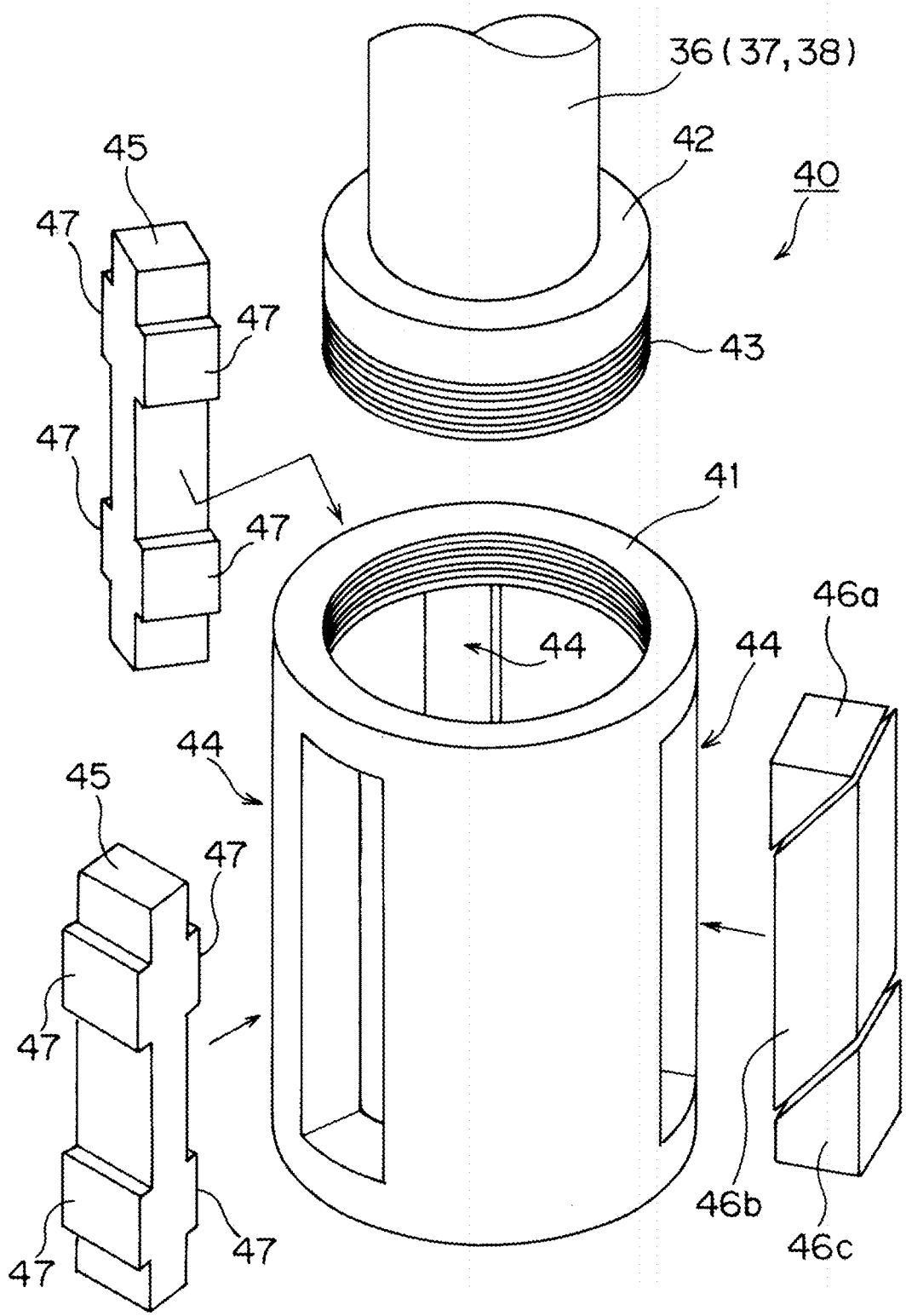
FIG. 11 is an exploded perspective view illustrating a support rod holding mechanism 40.
Figure 12:
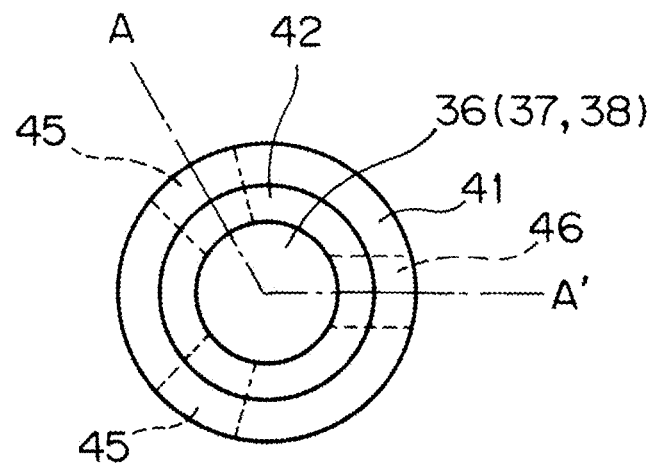
FIG. 12 is a schematic diagram illustrating a state where the support rod holding mechanism 40 is inserted into the base 31.
Figure 12:
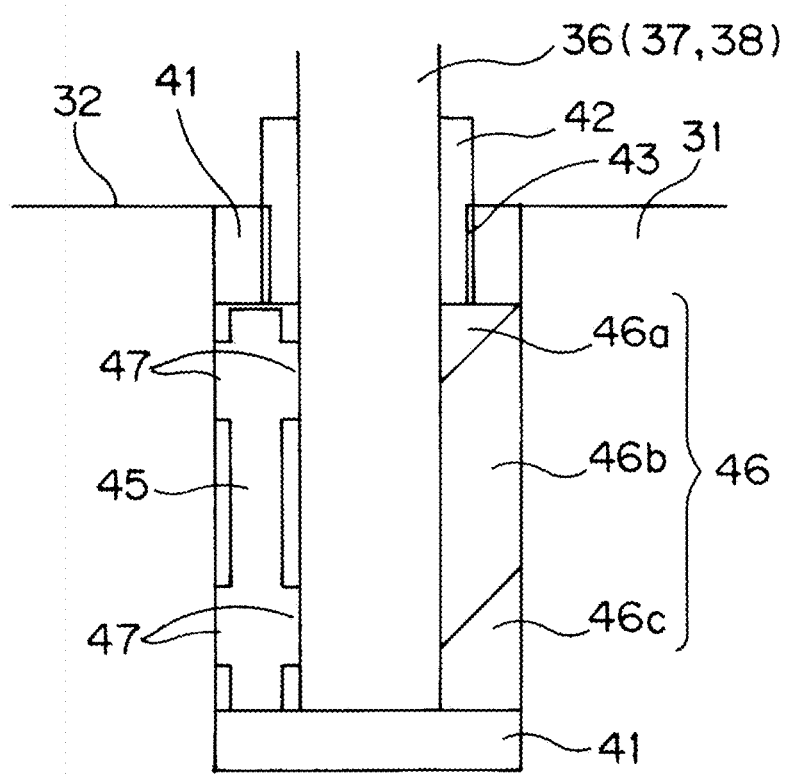

FIG. 11 is an exploded perspective view illustrating a support rod holding mechanism 40. FIG. 12 is a schematic diagram illustrating a state where the support rod holding mechanism 40 is inserted into the base 31. FIG. 12(*a*) is a plan view of the support rod holding mechanism 40, and FIG. 12(*b*) is an A-A' cross-sectional view in FIG. 12(*a*).

The support rod holding mechanism 40 includes a bottomed cylindrical member 41 provided with a space insertable with a support rod 36, 37, or 38, fixing blocks 45 and a load transmitting block 46 for constraining the support rod 36, 37, or 38, and a loading bolt 42 for applying a load on the fixing blocks 45 and the load transmitting block 46. In addition, since the support rods 36, 37, 38 are rod members having mutually different length but the same diameter, and will be described as the support rod 36 in the following description.

The inner wall of an opening of the cylindrical member 41 is formed with a female screw screwed with the below-described male screw part 43 provided on the outer circumference of the loading bolt 42. Also, in the side surface of the cylindrical member 41, through-holes 44 for arranging the fixing blocks 45 and the load transmitting block 46 are formed at regular intervals of approximately 120 degrees in three directions from a cylinder axis. In the through-holes 44 provided in three positions of the side surface of the cylindrical member 41, the two fixing blocks 45 and the one load transmitting block 46 are respectively arranged. The fixing blocks 45 are provided with convex parts 47 abutting on the support rod 36 at positions corresponding to the points 1 and 3 and the points 2 and 4 illustrated in FIG. 9. In addition, the fixing blocks 45 in the present embodiment are also provided with convex parts 47 at corresponding positions of a surface on the side opposite to the side abutting on the support rod 36.

The load transmitting block 46 is a wedge-shaped block described with reference to FIG. 10, includes three wedge-shaped members 46*a*, 46*b*, 46*c* mutually joined via a tilt surface, and is formed into a prism by combining the three wedge-shaped members 46*a*, 46*b*, 46*c* in such a manner as to bring their tilt surfaces into contact. When force in a compression direction along an axis of the prism is applied to the load transmitting block 46, the three wedge-shaped members 46*a*, 46*b*, 46*c* are mutually moved by sliding on the tilt surfaces.

The base 31 is provided with holes that are slightly larger than the outside diameter of the cylindrical member 41 and for receiving cylindrical members 41 and whose number is equal to the number of spheres 35 desired to be arranged in the XYZ space. In addition, the cylindrical members 41 are inserted into the respective holes of the base 31 with the load transmitting block 46 and the two fixing blocks 45 arranged in the through-holes 44.

The loading bolt 42 is a bolt-like member that is provided in the central part with a hole through which the support rod 36 is made to penetrate and whose outer circumferential part is provided with the male screw part 43 screwed into the female screw formed on the inner wall of the opening of the cylindrical member 41. The loading bolt 42 is different from general bolts in that the hole is formed in the central part, but adapted to be capable of being rotated by a wrench, which is a general tool, and attached to/detached from the cylindrical member 41 by forming parallel flat surfaces in parts where a male screw is not formed, or by other means.

When the loading bolt 42 is fastened to the cylindrical member 41, the load transmitting block 46 is applied with force along the long axis direction of the block. In the present embodiment, the length of the load transmitting block 46 in the long axis direction, in which the three wedge-shaped members 46*a*, 46*b*, 46*c* are combined, is made sufficiently larger than the length of the fixing blocks 45 in the long axis direction. In doing so, when the loading bolt 42 is fastened, the loading bolt 42 does not abut on the upper end parts of the fixing blocks 45, and a load at the time is transmitted only to the load transmitting block 46. In addition, regarding the fixing blocks 45 in the present embodiment, the upper end parts of the fixing blocks 45 are adapted not to abut on the loading bolt 42 at the time of fastening the loading bolt 42 by making the length in the long axis direction smaller than the length of the load transmitting block 46; however, the length in the long axis direction may be made the same as the load transmitting block 46, and in order that the upper end parts of the fixing blocks 45 lie outside the diameter of the loading bolt 42, the shape of the upper convex parts on the side abutting on the support rod 36 may be deformed.

The force applied to the load transmitting block 46 by fastening the loading bolt 42 is dispersed into horizontal force and vertical force with respect to the loading direction at the mutual joint part between the tilt surfaces of the wedge-shaped member 46*a* and wedge-shaped member 46*b* as described with reference to FIG. 10. Further, the vertical force is dispersed into horizontal force and vertical force with respect to the loading direction at the mutual joint part between the tilt surfaces of the wedge-shaped member 46b and wedge-shaped member 46c. Such bidirectional forces whose directions are different by 90 degrees allow the support rod 36 to be applied with force toward the central axis of the support rod 36 and downward force. The force toward the central axis of the support rod 36 is transmitted to the fixing blocks 45 installed in ±120-degree directions (see FIG. 12(*a*)) from the position where the load transmitting block 46 is arranged. In addition, the forces from the sides opposite to the abutting points between the convex parts 47 of the fixing blocks 45 and the support rod 36 constrain the support rod 36 on an X-Y plane. Also, the force downward of the support rod 36 is transmitted to the cylindrical member 41. Such motion in the Z axis direction that the lower end of the support rod 36 floats from the bottom of the cylindrical member 41 is constrained by the force in the same direction as the loading direction applied to the load transmitting block 46 at the time of fastening the loading bolt 42, which is force from the direction opposite to the motion. At this time, the wedge-shaped member 46a in direct contact with the loading bolt 42 slides and slightly moves to the support rod 36 side because of the tilts of the tilt surfaces with which the wedge-shaped member 46a and the wedge-shaped member 46b are in contact, and is thereby pressed against the outer circumferential surface of the support rod 36. The motion of the support rod 36 in the rotational direction is constrained by the frictional force between the outer circumferential surface of the support rod 36 and the surface of the wedge-shaped member 46a.

Also, in a state where the loading bolt 42 is fastened to the cylindrical member 41, among the wedge-shaped members 46a, 46b, 46c of the load transmitting block 46, the wedge-shaped member 46c arranged in contact with the bottom of the cylindrical member 41 slides and slightly move outward of the cylindrical member 41 because of the tilts of the tilt surfaces with which the wedge-shaped member 46b and the wedge-shaped member 46c are in contact. This allows the wedge-shaped member 46c to be pressed against the inner wall surface of the base 31 on the outer side than the outer circumference of the cylindrical member 41. At this time, the wedge-shaped member 46b tilts in association with the slight movements of the wedge-shaped member 46a and the wedge-shaped member 46c in the mutually opposite directions, and the upper edge is pressed against the inner wall surface of the base 31 on the outer side than the outer circumference of the cylindrical member 41. Also, as a material of the fixing blocks 45 and the load transmitting block 46, a soft metal as compared with iron is employed, such as aluminum, and therefore upon receipt of the load caused by fastening the loading bolt 42 via the load transmitting block 46, the fixing blocks 45 are pressed by the support rod 36 and thereby slightly deformed as well, and the convex parts 47 of the fixing blocks 45 on the side opposite to the convex parts 47 facing the support rod side are pressed against the inner wall surface of the base 31. By action of such force pressed against the inner wall of the base 31, the support rod holding mechanism 40 including the cylindrical member 41 is fixed to the base 31, and the support rod 36 is fixed to the base 31.

In addition, in the present embodiment, as the shape of the load transmitting block 46, the wedge-shaped one is employed; however, as long as a mechanism capable of dispersing a load from one direction in two directions, and applying lateral and downward forces to the support rod 36 is included, one of another shape may be employed.

Figure 13:
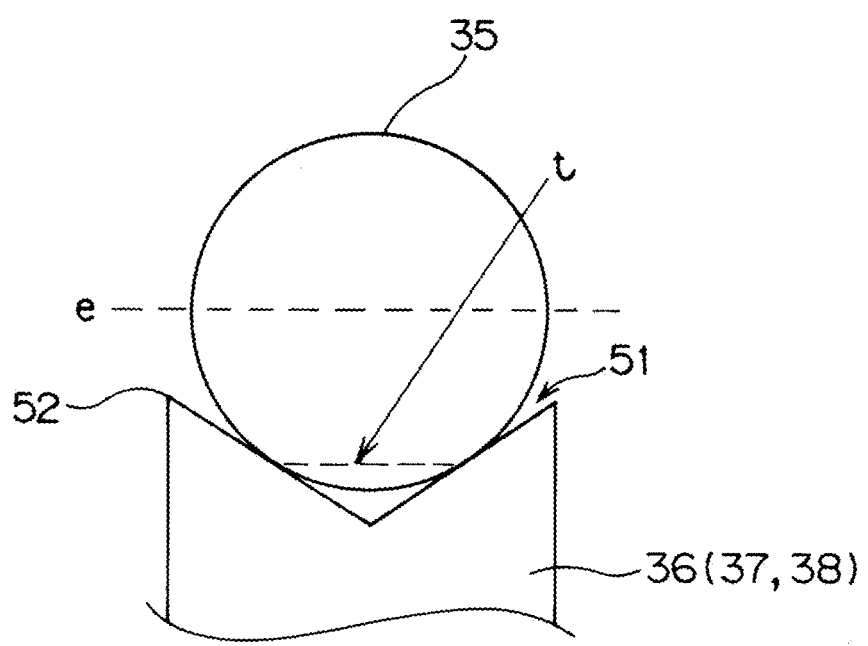
FIG. 13 is a schematic cross-sectional view illustrating the bonding structure of the sphere 35 at the tip of a support rod.

Next, a structure for fixing a sphere 35 to the tip of a support rod 36, 37, or 38 will be described. FIG. 13 is a schematic cross-sectional view illustrating the bonding structure of the sphere 35 at the tip of the support rod. The following description relates not only to the support rods 36, and the same applies to the support rods 37 and 38.

The one end (tip) of the support rod 36 in the present embodiment is applied with conical concave processing in order to firmly fix the sphere 35. The end part on the side opposite to the side where the sphere 35 is firmly fixed is formed in a flat shape contacting with the bottom surface of the cylindrical member 41. As illustrated in FIG. 13, when placing the sphere 35 on a conical concave part 51, the sphere 35 contacts with the conical tilt surface of the conical concave part 51 on a circular line indicated by sign t. The depth of the conical concave part 51 and the tilt of the conical surface are determined by the diameter of the sphere 35 so that the upper end 52 of the support rod 36, which is the edge of the conical concave part 51, lies closer to the apex side of the cone in the conical convex part 51 than the equator e of the sphere 35. The sphere 35 is fixed on the conical tilt surface of the conical concave part 51 by bond.

Figure 17:
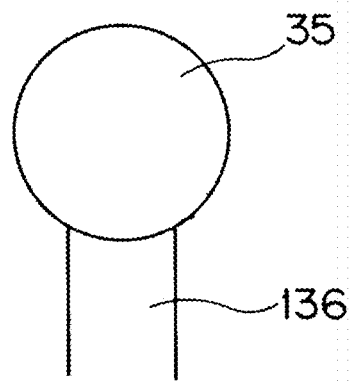
FIG. 17 is a schematic cross-sectional view illustrating conventional bonding structures of a sphere at the tip of a support rod.
Figure 17:
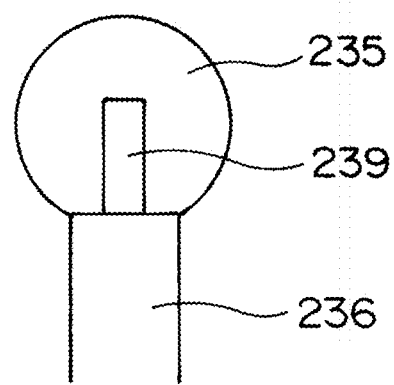

The sphere 35 is not required to be applied with hole drilling for inserting the thin shaft 239 as previously described with reference to FIG. 17(*a*), and on the equator e of the sphere 35, a structure that disturbs an X-ray transmission image is not present. For this reason, between the central position of an X-ray CT image of the sphere itself and the shape of the sphere, which are supposed to be detected, and the center position of an X-ray CT image of the sphere itself and the shape of the sphere, which are obtained by actual X-ray irradiation, no non-negligible deviation occurs.

Since the contact between the support rod 36 and the sphere 35 is limited to on the circular line of the conical tilt surface, difference in processing accuracy of each sphere 35 can be made less influential, and the attachment of the sphere 35 to the support rod 36 can be more stably performed than before. A certain clearance between the conical surface of the support rod 36 and an outer part of the sphere 35, which is not in direct contact, can also be filled with the bond, and therefore force for holding the sphere 35 can be stabilized.

Figure 14:
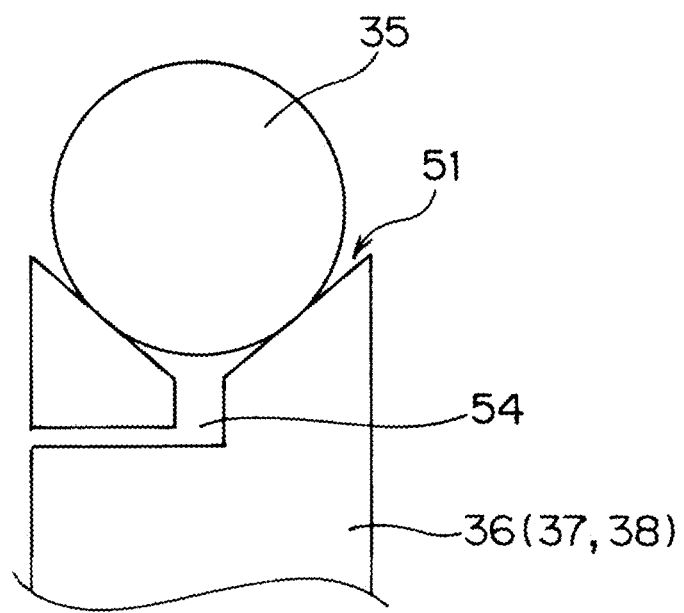
FIG. 14 is a schematic cross-sectional view illustrating the bonding structure of the sphere 35 at the tip of a support rod.

Another structure for fixing a sphere 35 to the tip of each support rod 36, 37, 38 will be described. FIG. 14 is a schematic cross-sectional view illustrating the bonding structure of the sphere 35 at the tip of the support rod. The following description relates not only to the support rods 36, and the same applies to the support rods 37 and 38.

At the tip of the support rod 36 illustrated in FIG. 14, a conical concave part 51 for placing the sphere 35 is formed as in the structure illustrated in FIG. 13. In addition, the tip of the support rod 36 illustrated in FIG. 14 is provided with a through-hole 54 passing from the bottom of the conical concave part 51 to the outer surface of the support rod 36. The through-hole 54 is one for allowing bond at the time of fixing the sphere 35 to escape to the outside of the conical concave part 51. By providing such a through-hole 54, the bond between a conical tilt surface and the sphere 35 can be thinned. Also, by a shrinking action when the bond cures, force for pulling the sphere 35 toward the bottom of the conical concave part 51 is generated to improve force for holding the sphere 35. In addition, an embodiment illustrated in FIG. 14 is adapted to allow the bond to more easily escape in such a manner that the through-hole 54 communicates to the outer surface of the support rod 36; however, the through-hole 54 is not necessarily required to be made penetrate to the outer surface of the support rod 36. Only by providing the bottom of the conical concave part 51 with a thin columnar concave part, the same degree of effect can be obtained.

Before performing X-ray CT imaging on the utensil 30, the coordinates of the 15 spheres 35 are measured by CMM, and information on the coordinates of the respective spheres 35 and the values of inter-sphere distances obtained from the results of the coordinate measurement are stored in the personal computer PC.

Also, in the utensil 30, the respective support rods 36, 37, 38 can be constrained in the three-dimensional space by the support rod holding mechanisms 40, and the spheres 35 are stably fixed to the respective support rods 36, 37, 38 formed with the conical concave parts 51. For this reason, even when the utensil 30 is tilted or turned upside down during transportation until the utensil 30 is placed on the rotation stage 13 or during installation, a change in sphere position can be reduced than before. Also, even when a significant amount of external force is applied to each support rod 36, 37, 38 because of the contact of the probe with a sphere 35 at the time of the coordinate measurement by the CMM, a sphere position can be prevented from being changed as conventional.

After the end of the coordinate measurement by the CMM, the XYZ space in which the respective spheres 35 are arranged is covered with the cover 33. In the utensil 30, the number of spheres 35 is suppressed to 15, and therefore the coordinate measurement by the CMM can be quickly performed. Further, the number of parts can be reduced than before, and therefore the fabrication cost of the utensil 30 can also be suppressed.

When performing the X-ray CT imaging on the utensil 30, the utensil 30 is positioned with the cover 33 attached on the rotation stage 13, and the X-ray CT imaging is performed.

In the utensil 30 of the present embodiment, as illustrated in FIG. 4, the projection coordinates (Xi, Yi) of the respective spheres 35 are almost uniform, and the positions of the three X-Y planes having different Z positions are also almost uniform in the Z direction, so that the 15 spheres 35 arranged in the XYZ space are not structured such that they are arranged on conical surfaces as conventional, and respectively have appropriate distance intervals. Such sphere arrangement enables spatial distortion specific to an X-ray CT device to be sufficiently captured.

In the utensil 30 of the present embodiment, by forming the upper surface of the base 31 as the flat surface 32, and differentiating the lengths of the support rods 36, 37, 38 supporting the spheres 35, an evaluation range in the Z axis direction in an imaging visual space by one time of X-ray CT imaging can be more widened than in a conventional utensil having a step-wise base.

Also, in the utensil 30 of the present embodiment, the difference in length (e.g., 60 mm) between the support rod 36 having the shortest length and the support rod 38 having the longest length is made longer than the radius (50 mm) of the circle around the origin (0, 0) of the projection coordinates illustrated in FIG. 4. For this reason, the arrangement range of the multiple spheres is such that among the multiple X-Y planes, the distance in the Z direction between the X-Y plane having the lowest Z position and the X-Y plane having the highest Z position is larger than the distance from the Z axis in the XY directions. As described, in the present embodiment, the difference between the arrangement range of the spheres 35 in the X-Y planes and the arrangement range in the Z axis direction is made smaller than before, and therefore, for example, when the ratio between the vertical and horizontal sizes of the X-ray detector 12 is one, the cylindrical imaging visual space can be isotropically evaluated by two times of X-ray CT imaging, and when the ratio between the vertical and horizontal sizes of the X-ray detector 12 is vertical:horizontal=1:2, the cylindrical imaging visual space can be isotropically evaluated by one time of X-ray CT imaging. As described, the number of times of performing repeated measurement with a Z axis position changed can be reduced than before, and therefore imaging time for evaluating the measurement accuracy of an X-ray CT device can be reduced.

In addition, in order to make it possible to isotropically evaluate the cylindrical imaging visual space by one time of X-ray CT imaging, when the ratio between the vertical and horizontal sizes of the X-ray detector 12 is one, among the multiple X-Y planes, the distance in the Z direction between the X-Y plane having the lowest Z position and the X-Y plane having the highest Z position, and a distance twice as long as the distance from the Z axis in the XY directions are preferably almost the same. The arrangement range of the spheres 35 is only required to be changed depending on the size of the X-ray detector 12, the bending length of the material of the support rods 36, 37, 38, and the like in a range where among the multiple X-Y planes, the distance in the Z direction between the X-Y plane having the lowest Z position and the X-Y plane having the highest Z position is larger than the distance from the Z axis in the XY directions (the radius of the circle around the origin (0, 0) of the projection coordinates illustrated in FIG. 4) and smaller than or almost equal to twice as long as the distance from the Z axis in the XY directions (the diameter of the circle around the origin (0, 0) of the projection coordinates illustrated in FIG. 4).

The invention claimed is:

1. A utensil for evaluating a length measurement error in an X-ray CT device for three-dimensional shape measurement, the utensil comprising:
   a base;
   multiple spheres arranged in an XYZ space on the base; and
   multiple support rods supporting each of the multiple spheres and installed upright on the base, wherein
   in the XYZ space on the base, multiple spheres having different Z positions are arranged, and
   among the multiple spheres,
   one or more spheres are arranged in a vicinity of a Z axis, and
   in each of multiple X-Y planes having different Z positions, multiple outer circumference side spheres are arranged along one outer circumference.

2. The utensil for evaluating a length measurement error in an X-ray CT device for three-dimensional shape measurement according to claim 1, wherein outer circumference side spheres arranged in each of the multiple X-Y planes are cylindrically arranged.

3. The utensil for evaluating a length measurement error in an X-ray CT device for three-dimensional shape measurement according to claim 1, wherein the spheres arranged in the vicinity of the Z axis are multiple inner circumference side spheres.

4. The utensil for evaluating a length measurement error in an X-ray CT device for three-dimensional shape measurement according to claim 3, wherein a distance between the inner circumference side spheres and the Z axis is set to be 20% or less of a distance between the outer circumference side spheres and the Z axis.

5. The utensil for evaluating a length measurement error in an X-ray CT device for three-dimensional shape measurement according to claim 1, wherein in each of the multiple X-Y planes, multiple outer circumference side spheres and one or more inner circumference side spheres are arranged.

6. The utensil for evaluating a length measurement error in an X-ray CT device for three-dimensional shape measurement according to claim 1, wherein an arrangement range of the multiple spheres is a range where a distance in a Z direction between an X-Y plane having a lowest Z position and an X-Y plane having a highest Z position among the multiple X-Y planes is larger than a distance from the Z axis in XY directions.

7. The utensil for evaluating a length measurement error in an X-ray CT device for three-dimensional shape measurement according to claim 1, wherein the outer circumference side spheres are arranged in such a manner that an average value of distances between respective outer circumference side spheres in each of the X-Y planes and the Z axis is equal among the multiple X-Y planes.

8. The utensil for evaluating a length measurement error in an X-ray CT device for three-dimensional shape measurement according to claim 1, wherein the multiple X-Y planes are at least three X-Y planes whose mutual distances in a Z direction are equally separated.

9. The utensil for evaluating a length measurement error in an X-ray CT device for three-dimensional shape measurement according to claim 1, wherein as arrangement of the outer circumference side spheres,
multiple sets of two spheres separated from the Z axis by a predetermined distance and oppositely arranged with respect to the Z axis are arranged in each of the multiple X-Y planes having different Z positions, and thereby at least four are arranged in each of the X-Y planes.

10. The utensil for evaluating a length measurement error in an X-ray CT device for three-dimensional shape measurement according to claim 9, wherein the multiple X-Y planes are at least three X-Y planes whose mutual distances in a Z direction are equally separated, and
among the multiple spheres, multiple sets of two spheres oppositely arranged with respect to the Z axis are arranged, and thereby spheres arranged in each of the three X-Y planes are equally arranged at intervals of substantially 30 degrees on a circle around the Z axis in a plan view where the three X-Y planes are superposed.

11. The utensil for evaluating a length measurement error in an X-ray CT device for three-dimensional shape measurement according to claim 9, wherein in each of the multiple X-Y planes, one or more inner circumference side spheres are also arranged, and
the one or more inner circumference side spheres are arranged on lines connecting the outer circumference side spheres that are oppositely arranged.

12. The utensil for evaluating a length measurement error in an X-ray CT device for three-dimensional shape measurement according to claim 1, wherein the outer circumference side spheres are arranged at regular intervals on a circle around the Z axis in a plan view of one X-Y plane.

13. The utensil for evaluating a length measurement error in an X-ray CT device for three-dimensional shape measurement according to claim 1, wherein the base has a flat surface on a top thereof, and
the lengths of the multiple support rods are different each other so that the Z positions of the arranged multiple spheres are different each other.

14. The utensil for evaluating a length measurement error in an X-ray CT device for three-dimensional shape measurement according to claim 1, wherein
the multiple support rods are respectively provided with support rod holding mechanisms inserted into holes that are formed in the base so as to correspond to the number of the multiple support rods, and
each of the support rod holding mechanisms comprises:
a bottomed cylindrical member that is inserted into one of the holes of the base, whose side surface is provided with multiple through-holes, and that is provided with a space into which one of the support rods is inserted;
a loading bolt whose central part is provided with a hole through which the support rod is made to penetrate and whose outer circumferential part is provided with a male screw part screwed into a female screw formed on an inner wall of an opening of the cylindrical member;
fixing block inserted into one of the through-holes of the cylindrical member and having a convex part that abuts on a side surface of the support rod whose end part on a side opposite to a side where a sphere is supported abuts on a bottom of the cylindrical member, and
a load transmitting block that is inserted into one of the through-holes of the cylindrical member and in two directions, transmits force generated when the loading bolt is fastened to the cylindrical member by screwing the female screw and the male screw part together, the two directions being a direction to constrain a degree of freedom of the support rod in a translation direction in an X-Y plane and a direction to constrain a degree of freedom of the support rod in a translation direction on the Z axis.

15. The utensil for evaluating a length measurement error in an X-ray CT device for three-dimensional shape measurement according to claim 14, wherein the through-holes of the cylindrical member are provided in three positions of the side surface of the cylindrical member at regular intervals around a cylinder axis, and
in two of the through-holes, the fixing blocks are arranged, and in one, the load transmitting block is arranged.

16. The utensil for evaluating a length measurement error in an X-ray CT device for three-dimensional shape measurement according to claim 14, wherein the load transmitting block includes three wedge-shaped members mutually joined via a tilt surface.

17. The utensil for evaluating a length measurement error in an X-ray CT device for three-dimensional shape measurement according to claim 1, wherein one end of each of the support rods is provided with a conical concave part, and a sphere is supported in contact with a conical tilt surface of the conical concave part.

18. The utensil for evaluating a length measurement error in an X-ray CT device for three-dimensional shape measurement according to claim 17, wherein a bottom of the conical concave part of the support rod is provided with a through-hole.

* * * * *